US008438898B2

(12) United States Patent
Petisce et al.

(10) Patent No.: US 8,438,898 B2
(45) Date of Patent: May 14, 2013

(54) CALIBRANT INFUSION FLUID SOURCE PREPARATION

(75) Inventors: James R. Petisce, San Clemente, CA (US); Michael J. Higgins, Huntington Beach, CA (US); Kristie Trinh, Pico Rivera, CA (US); Todd Abraham, Mission Viejo, CA (US)

(73) Assignee: Edwards Lifesciences Corporation, Irvine, CA (US)

( * ) Notice: Subject to any disclaimer, the term of this patent is extended or adjusted under 35 U.S.C. 154(b) by 393 days.

(21) Appl. No.: 12/827,802

(22) Filed: Jun. 30, 2010

(65) Prior Publication Data

US 2011/0154880 A1  Jun. 30, 2011

Related U.S. Application Data

(60) Provisional application No. 61/222,425, filed on Jul. 1, 2009.

(51) Int. Cl.
  *G01N 31/22*  (2006.01)
  *G01N 33/66*  (2006.01)
  *G01N 33/96*  (2006.01)

(52) U.S. Cl.
  USPC ............ 73/1.03; 600/347; 600/635; 600/309; 436/8; 436/11; 436/14; 436/18

(58) Field of Classification Search ............... 73/1.02, 73/1.03; 600/347, 345, 635, 309; 436/8, 11, 436/14, 18
  See application file for complete search history.

(56) References Cited

U.S. PATENT DOCUMENTS

| 4,633,878 | A | 1/1987 | Bombardieri |
| 5,330,634 | A | 7/1994 | Wong et al. |
| 5,976,085 | A * | 11/1999 | Kimball et al. ............... 600/309 |
| 6,399,110 | B1 | 6/2002 | Kikuchi et al. |
| 6,599,746 | B1 * | 7/2003 | Gumbrecht ..................... 436/19 |
| 7,171,252 | B1 * | 1/2007 | Scarantino et al. ........... 600/345 |
| 7,422,903 | B2 * | 9/2008 | Conlon et al. .................... 436/8 |
| 7,715,893 | B2 * | 5/2010 | Kamath et al. ................ 600/347 |
| 7,920,960 | B2 * | 4/2011 | Liu et al. ....................... 701/118 |
| 2005/0074893 | A1 | 4/2005 | Horiguchi et al. |
| 2006/0009727 | A1 | 1/2006 | O'Mahony et al. |
| 2007/0027384 | A1 | 2/2007 | Brister |
| 2008/0208173 | A1 | 8/2008 | Lee et al. |
| 2010/0217238 | A1 * | 8/2010 | DeJournett ............... 604/890.1 |

OTHER PUBLICATIONS

International Search Report, Mar. 14, 2011.

* cited by examiner

*Primary Examiner* — Peter Macchiarolo
*Assistant Examiner* — Rose M Miller
(74) *Attorney, Agent, or Firm* — Michael Crapenhoft

(57) ABSTRACT

Methods and systems for preparation of calibrant infusion fluid sources are disclosed. In one embodiment, a precise volume of glucose is injected into a saline-solution filled calibrant infusion fluid source proximate in time to conducting a calibration procedure. The glucose concentration in the calibrant infusion fluid source is subsequently calculated based on the measured weight of the saline-solution, as determined prior to glucose injection, and the volume of glucose injected. This method provides a highly accurate and convenient manner for use in a hospital environment, for example, with an intravenous blood glucose sensor system. In another embodiment, a premixed calibrant infusion fluid source is provided that includes saline solution and a predetermined concentration of glucose. In such embodiments, shelf life problems related to water evaporation are mitigated by hermetically covering or otherwise hermetically containing the calibrant infusion fluid source up until the point of use.

20 Claims, 19 Drawing Sheets

| Bag | Weight (g) | Bag Adj Weight (Weight - 17 g) | YSI 1 (mg/dL) | YSI 2 (mg/dL) | YSI 3 (mg/dL) | YSI mean (mg/dL) | YSI Std Dev | YSI % Std Dev | Bag Adj Glucose (mg/dL) | Δ, YSI-Bag Adj Glucose | %Δ, Δ/200 | |
|---|---|---|---|---|---|---|---|---|---|---|---|---|
| 1 | 558 | 541 | 201 | 201 | 201 | 201.0 | 0.00 | 0.00% | 198.2 | 2.8 | 1.4% | |
| 2 | 559 | 542 | 191 | 190 | 189 | 190.0 | 1.00 | 0.53% | 197.8 | -7.8 | -3.9% | |
| 3 | 560 | 543 | 200 | 196 | 198 | 198.0 | 2.00 | 1.01% | 197.5 | 0.5 | 0.3% | |
| 4 | 559 | 542 | 200 | 201 | 201 | 200.7 | 0.58 | 0.29% | 197.8 | 2.8 | 1.4% | |
| 5 | 561 | 544 | 203 | 201 | 201 | 201.7 | 1.15 | 0.57% | 197.1 | 4.6 | 2.3% | |
| 6 | 558 | 541 | 207 | 205 | 206 | 206.0 | 1.00 | 0.49% | 198.2 | 7.8 | 3.9% | |
| 7 | 559 | 542 | 205 | 204 | 205 | 204.7 | 0.58 | 0.28% | 197.8 | 6.8 | 3.4% | |
| 8 | 561 | 544 | 210 | 209 | 209 | 209.3 | 0.58 | 0.28% | 197.1 | 12.2 | 6.1% | |
| 9 | 560 | 543 | 203 | 201 | 201 | 201.7 | 1.15 | 0.57% | 197.5 | 4.2 | 2.1% | |
| 10 | 560 | 543 | 202 | 201 | 202 | 201.7 | 0.58 | 0.29% | 197.5 | 4.2 | 2.1% | |
| 11 | 555 | 538 | 206 | 203 | 202 | 203.7 | 2.08 | 1.02% | 199.3 | 4.4 | 2.2% | |
| 12 | 560 | 543 | 202 | 202 | 205 | 203.0 | 1.73 | 0.85% | 197.5 | 5.5 | 2.8% | |
| 13 | 560 | 543 | 204 | 204 | 204 | 204.0 | 0.00 | 0.00% | 197.5 | 6.5 | 3.3% | |
| 14 | 562 | 545 | 206 | 207 | 207 | 206.7 | 0.58 | 0.28% | 196.7 | 9.9 | 5.0% | |
| 16 | 560 | 543 | 227 | 227 | 227 | 227.0 | 0.00 | 0.00% | 197.5 | 29.5 | 14.8% | |
| 17 | 559 | 542 | 207 | 208 | 210 | 208.3 | 1.53 | 0.73% | 197.8 | 10.5 | 5.2% | |
| 18 | 558 | 541 | 232 | 232 | 233 | 232.3 | 0.58 | 0.25% | 198.2 | 34.1 | 17.1% | |
| 19 | 561 | 544 | 207 | 207 | 205 | 206.3 | 1.15 | 0.56% | 197.1 | 9.2 | 4.6% | |
| 20 | 557 | 540 | 216 | 214 | 213 | 214.3 | 1.53 | 0.71% | 198.6 | 15.8 | 7.9% | |
| 21 | 557 | 540 | 208 | 211 | 209 | 209.3 | 1.53 | 0.73% | 198.6 | 10.8 | 5.4% | |
| 22 | 558 | 541 | 232 | 231 | 232 | 231.7 | 0.58 | 0.25% | 198.2 | 33.5 | 16.7% | |
| 23 | 559 | 542 | 211 | 212 | 208 | 210.3 | 2.08 | 0.99% | 197.8 | 12.5 | 6.2% | |
| 24 | 557 | 540 | 212 | 214 | 210 | 212.0 | 2.00 | 0.94% | 198.6 | 13.4 | 6.7% | |
| 25 | 559 | 542 | 204 | 207 | 206 | 205.7 | 1.53 | 0.74% | 197.8 | 7.8 | 3.9% | |
| | | | | | Mean | 207.89 | 1.06 | 0.52% | 197.8 | 10.06 | 5.03% | Mean |
| Mean | 559.0 | 542.0 | | | Std Dev | 10.02 | 0.67 | 0.325% | 0.59 | 34.13 | 17.07% | High |
| Std Dev | 1.60 | 1.60 | | | % Std Dev | 4.82% | 62.70% | 63.08% | 0.30% | -7.84 | -3.92% | Low |
| % Std Dev | 0.29% | 0.30% | | | | | | | | | | |

FIG. 8

| Bag | Weight (g) | Bag Adj Weight (Weight - 17 g) | YSI 1 (mg/dL) | YSI 2 (mg/dL) | YSI 3 (mg/dL) | YSI mean (mg/dL) | YSI Std Dev | YSI % Std Dev | Bag Adj Glucose (mg/dL) | $\Delta$, YSI-Bag Adj Glucose | %$\Delta$, $\Delta$/200 |
|---|---|---|---|---|---|---|---|---|---|---|---|
| 30 | 563 | 546 | 188 | 184 | 186 | 186.0 | 2.00 | 0.00% | 196.4 | -10.4 | -5.2% |
| 31 | 559 | 542 | 189 | 194 | 191 | 191.3 | 2.52 | 1.32% | 197.8 | -6.5 | -3.3% |
| 32 | 557 | 540 | 187 | 190 | 188 | 188.3 | 1.53 | 0.81% | 198.6 | -10.2 | -5.1% |
| 33 | 563 | 546 | 188 | 187 | 188 | 187.7 | 0.58 | 0.31% | 196.4 | -8.7 | -4.4% |
| 34 | 561 | 544 | 193 | 191 | 188 | 190.7 | 2.52 | 1.32% | 197.1 | -6.4 | -3.2% |
| 35 | 560 | 543 | 190 | 189 | 189 | 189.3 | 0.58 | 0.30% | 197.5 | -8.1 | -4.1% |
| 36 | 560 | 543 | 190 | 189 | 189 | 189.3 | 0.58 | 0.30% | 197.5 | -8.1 | -4.1% |
| 37 | 558 | 541 | 191 | 192 | 189 | 190.7 | 1.53 | 0.80% | 198.2 | -7.5 | -3.8% |
| 38 | 559 | 542 | 189 | 190 | 191 | 190.0 | 1.00 | 0.53% | 197.8 | -7.8 | -3.9% |
| 39 | 561 | 544 | 189 | 191 | 190 | 190.0 | 1.00 | 0.53% | 197.1 | -7.1 | -3.6% |
| 40 | 561 | 544 | 188 | 185 | 186 | 186.3 | 1.53 | 0.82% | 197.1 | -10.8 | -5.4% |
| 41 | 561 | 544 | 186 | 187 | 189 | 187.3 | 1.53 | 0.82% | 197.1 | -9.8 | -4.9% |
| 42 | 558 | 541 | 190 | 191 | 187 | 189.3 | 2.08 | 0.00% | 198.2 | -8.9 | -4.4% |
| 43 | 558 | 541 | 187 | 190 | 188 | 188.3 | 1.53 | 0.81% | 198.2 | -9.9 | -4.9% |
| 44 | 558 | 541 | 190 | 191 | 189 | 190.0 | 1.00 | 0.00% | 198.2 | -8.2 | -4.1% |
| 45 | 560 | 543 | 189 | 192 | 188 | 189.7 | 2.08 | 1.10% | 197.5 | -7.8 | -3.9% |
| 46 | 561 | 544 | 190 | 188 | 189 | 189.0 | 1.00 | 0.53% | 197.1 | -8.1 | -4.1% |
| 47 | 558 | 541 | 189 | 192 | 190 | 190.3 | 1.53 | 0.80% | 198.2 | -7.9 | -3.9% |
| 48 | 558 | 541 | 191 | 189 | 191 | 190.3 | 1.15 | 0.61% | 198.2 | -7.9 | -3.9% |
| 49 | 559 | 542 | 187 | 189 | 187 | 187.7 | 1.15 | 0.62% | 197.8 | -10.2 | -5.1% |
| 50 | 555 | 538 | 195 | 190 | 190 | 191.7 | 2.89 | 1.51% | 199.3 | -7.6 | -3.8% |
| Mean | 559.4 | 542.4 | | | Mean | 189.21 | 1.49 | 0.66% | 197.7 | -8.48 | -4.24% | Mean |
| Std Dev | 1.96 | 1.96 | | | Std Dev | 1.55 | 0.66 | 0.43% | 0.72 | -6.44 | -3.22% | High |
| % Std Dev | 0.35% | 0.36% | | | % Std Dev | 0.82% | 44.29% | 64.90% | 0.36% | -10.78 | -5.39% | Low |

FIG. 9

| Bag | Weight (g) | Bag Adj Weight (Weight - 17 g) | Bag Adj Glucose (mg/dL) | YSI 1 (mg/dL) | YSI 2 (mg/dL) | YSI 3 (mg/dL) | YSI mean (mg/dL) | YSI Std Dev | YSI % Std Dev | Δ, YSI-Bag Adj Glucose | %Δ, Δ/(200 mg/dL) | Gem 1 (mg/dL) | Gem 2 (mg/dL) | Gem 3 (mg/dL) | GEM Mean (mg/dL) | GEM Std Dev | GEM % Std Dev | Δ, GEM-Calculated Glucose | %Δ, Δ/(200 mg/dL) |
|---|---|---|---|---|---|---|---|---|---|---|---|---|---|---|---|---|---|---|---|
| 1 | 558 | 541 | 198.2 | 201 | 201 | 201 | 201.0 | 0.00 | 0.00% | 2.8 | 1.4% | | | | | | | | |
| 2 | 559 | 542 | 197.8 | 191 | 190 | 189 | 190.0 | 1.00 | 0.53% | -7.8 | -3.9% | | | | | | | | |
| 3 | 560 | 543 | 197.5 | 200 | 196 | 198 | 198.0 | 2.00 | 1.01% | 0.5 | 0.3% | | | | | | | | |
| 4 | 559 | 542 | 197.8 | 209 | 201 | 201 | 203.7 | 0.58 | 0.29% | 2.8 | 1.4% | | | | | | | | |
| 5 | 561 | 544 | 197.1 | 203 | 201 | 201 | 201.7 | 1.15 | 0.57% | 4.6 | 2.3% | 210 | 210 | 211 | 210.3 | 0.6 | 0.3% | 12.5 | 6.2% |
| 6 | 558 | 541 | 199.2 | 207 | 205 | 206 | 206.0 | 1.00 | 0.49% | 7.8 | 3.9% | 211 | 212 | 214 | 212.3 | 1.5 | 0.7% | 15.2 | 7.6% |
| 7 | 559 | 542 | 197.8 | 205 | 204 | 205 | 204.7 | 0.58 | 0.28% | 6.8 | 3.4% | 215 | 217 | 217 | 216.3 | 1.2 | 0.5% | 18.1 | 9.1% |
| 8 | 561 | 544 | 197.1 | 210 | 209 | 209 | 209.3 | 0.58 | 0.28% | 12.2 | 6.1% | 217 | 217 | 218 | 217.3 | 0.6 | 0.3% | 19.5 | 9.7% |
| 9 | 560 | 543 | 197.5 | 203 | 201 | 201 | 201.7 | 1.15 | 0.57% | 4.2 | 2.1% | 226 | 225 | 227 | 226.0 | 1.0 | 0.4% | 28.9 | 14.4% |
| 10 | 560 | 543 | 197.5 | 202 | 201 | 201 | 201.7 | 0.58 | 0.29% | 4.2 | 2.1% | 219 | 220 | 219 | 219.3 | 0.6 | 0.3% | 21.9 | 10.9% |
| 11 | 555 | 538 | 199.3 | 206 | 203 | 202 | 203.7 | 2.08 | 1.02% | 4.4 | 2.2% | 221 | 222 | 215 | 219.3 | 3.8 | 1.7% | 21.9 | 10.9% |
| 12 | 560 | 543 | 197.5 | 202 | 202 | 205 | 203.0 | 1.73 | 0.85% | 5.5 | 2.8% | 215 | 218 | 217 | 216.7 | 1.5 | 0.7% | 17.4 | 8.7% |
| 13 | 560 | 543 | 197.5 | 204 | 204 | 204 | 204.0 | 0.00 | 0.00% | 6.5 | 3.3% | 216 | 214 | 216 | 215.3 | 1.2 | 0.5% | 17.9 | 8.9% |
| 14 | 562 | 545 | 196.7 | 206 | 207 | 207 | 206.7 | 0.58 | 0.28% | 9.9 | 5.0% | 215 | 216 | | 215.5 | 0.7 | 0.3% | 18.0 | 9.0% |
| 15 | 560 | 543 | 197.5 | 227 | 227 | 227 | 227.0 | 0.00 | 0.00% | 29.5 | 14.8% | 217 | 217 | | 217.0 | 0.0 | 0.0% | 20.3 | 10.1% |
| 16 | 560 | 543 | 197.8 | 207 | 203 | 210 | 206.3 | 1.53 | 0.73% | 10.5 | 5.2% | 235 | 238 | 239 | 237.7 | 1.5 | 0.6% | 40.2 | 20.1% |
| 17 | 559 | 542 | 197.8 | 207 | 203 | 210 | 206.3 | — | — | — | — | 218 | 219 | | 218.5 | 0.7 | 0.3% | 20.7 | 10.3% |
| 18 | 558 | 541 | 198.2 | 232 | 232 | 233 | 232.3 | 0.58 | 0.25% | 34.1 | 17.1% | 246 | 246 | | 246.0 | 0.0 | 0.0% | 47.8 | 23.9% |
| 19 | 561 | 544 | 197.1 | 207 | 207 | 205 | 206.3 | 1.15 | 0.56% | 9.2 | 4.6% | 218 | 214 | 219 | 216.0 | 2.8 | 1.3% | 18.9 | 9.4% |
| 20 | 557 | 540 | 198.5 | 216 | 214 | 213 | 214.3 | 1.53 | 0.71% | 15.8 | 7.9% | 218 | 219 | 215 | 218.5 | 0.7 | 0.3% | 19.9 | 10.0% |
| 21 | 557 | 540 | 198.6 | 208 | 211 | 209 | 209.3 | 1.53 | 0.73% | 10.8 | 5.4% | 217 | 217 | 217 | 217.0 | 0.0 | 0.0% | 18.4 | 9.2% |
| 22 | 558 | 541 | 198.2 | 232 | 231 | 232 | 231.7 | 0.58 | 0.25% | 33.5 | 16.7% | 240 | 239 | | 239.5 | 0.7 | 0.3% | 41.3 | 20.6% |
| 23 | 559 | 542 | 197.8 | 211 | 212 | 208 | 210.3 | 2.08 | 0.99% | 12.5 | 6.2% | 217 | 217 | | 217.0 | 0.0 | 0.0% | 19.2 | 9.6% |
| 24 | 557 | 540 | 198.6 | 212 | 214 | 210 | 212.0 | 2.00 | 0.94% | 13.4 | 6.7% | 216 | 216 | | 216.0 | 0.0 | 0.0% | 17.4 | 8.7% |
| 25 | 559 | 542 | 197.8 | 204 | 207 | 206 | 205.7 | 1.53 | 0.74% | 7.8 | 3.9% | 218 | 218 | | 218.0 | 0.0 | 0.0% | 20.2 | 10.1% |
| Mean | 559.3 | 542.3 | 197.8 | | | | 207.89 | 1.06 | 0.52% | 10.06 | 5.03% | | | Mean | 220.5 | 0.9 | 0.4% | 22.64 | 11.3% |
| Std Dev | 1.60 | 1.60 | 0.59 | | | Std Dev | 10.02 | 0.67 | 0.325% | 34.13 | 17.07% | | | Std Dev | 9.20 | 0.97 | 0.004 | 47.80 | 23.9% | High |
| % Std Dev | 0.29% | 0.30% | 0.30% | | | % Std Dev | 4.82% | 62.70% | 63.08% | -7.54 | -3.92% | Low | | % Std Dev | 4.17% | 106.5% | 106.9% | 12.50 | 6.25% | Low |

FIG. 14

| Bag | Weight (g) | Bag Adj Weight (Weight - 17 g) | Bag Adj Glucose (mg/dL) | YSI 1 (mg/dL) | YSI 2 (mg/dL) | YSI 3 (mg/dL) | YSI mean (mg/dL) | YSI Std Dev (mg/dL) | YSI % Std Dev | Δ YSI-Bag Adj Glucose | %Δ, Δ/(200 mg/dL) | | Gem 1 (mg/dL) | Gem 2 (mg/dL) | Gem 3 (mg/dL) | GEM Mean (mg/dL) | GEM Std Dev (mg/dL) | GEM % Std Dev | Δ, GEM-Calculated Glucose | %Δ, Δ/(200 mg/dL) |
|---|---|---|---|---|---|---|---|---|---|---|---|---|---|---|---|---|---|---|---|---|
| 30 | 563 | 546 | 196.4 | 188 | 184 | 186 | 186.0 | 2.00 | 0.00% | -10.4 | -5.2% | | 198 | 197 | 197 | 197.3 | 0.58 | 0.3% | 0.9 | 0.47% |
| 31 | 559 | 542 | 197.8 | 189 | 194 | 191 | 191.3 | 2.52 | 1.32% | -6.5 | -3.3% | | 202 | 195 | 193 | 196.7 | 4.73 | 2.4% | -1.2 | -0.59% |
| 32 | 557 | 540 | 198.6 | 187 | 190 | 188 | 188.3 | 1.53 | 0.81% | -10.2 | -5.1% | | 192 | 191 | 190 | 191.0 | 1.00 | 0.5% | -7.6 | -3.79% |
| 33 | 563 | 546 | 196.4 | 188 | 187 | 188 | 187.7 | 0.58 | 0.31% | -8.7 | -4.4% | | 188 | 189 | 189 | 188.7 | 0.58 | 0.3% | -7.7 | -3.85% |
| 34 | 561 | 544 | 197.1 | 193 | 191 | 188 | 190.7 | 2.52 | 1.32% | -6.4 | -3.2% | | 194 | 193 | 193 | 193.3 | 0.58 | 0.3% | -3.8 | -1.89% |
| 35 | 560 | 543 | 197.5 | 190 | 189 | 189 | 189.3 | 0.58 | 0.30% | -8.1 | -4.1% | | 191 | 192 | 192 | 191.7 | 0.58 | 0.3% | -5.8 | -2.90% |
| 36 | 560 | 543 | 197.5 | 190 | 189 | 189 | 189.3 | 0.58 | 0.30% | -8.1 | -4.1% | | 191 | 190 | 192 | 191.0 | 1.00 | 0.5% | -6.5 | -3.24% |
| 37 | 558 | 541 | 198.2 | 191 | 192 | 189 | 190.7 | 1.53 | 0.80% | -7.5 | -3.8% | | 190 | 192 | 191 | 191.0 | 1.00 | 0.5% | -7.2 | -3.60% |
| 38 | 559 | 542 | 197.8 | 189 | 190 | 191 | 190.0 | 1.00 | 0.53% | -7.8 | -3.9% | | 189 | 190 | 190 | 189.7 | 0.58 | 0.3% | -8.2 | -4.09% |
| 39 | 561 | 544 | 197.1 | 189 | 191 | 190 | 190.0 | 1.00 | 0.53% | -7.1 | -3.6% | | 191 | 192 | 191 | 191.3 | 0.58 | 0.3% | -5.8 | -2.89% |
| 40 | 561 | 544 | 197.1 | 188 | 185 | 186 | 186.3 | 1.53 | 0.82% | -10.8 | -5.4% | | 188 | 186 | 185 | 186.3 | 1.53 | 0.8% | -10.8 | -5.39% |
| 41 | 561 | 544 | 197.1 | 186 | 187 | 189 | 187.3 | 1.53 | 0.82% | -9.8 | -4.9% | | 188 | 191 | 188 | 189.0 | 1.73 | 0.9% | -8.1 | -4.06% |
| 42 | 559 | 541 | 198.2 | 190 | 191 | 187 | 189.3 | 2.08 | 0.00% | -8.9 | -4.4% | | 191 | 191 | 191 | 191.0 | 0.00 | 0.0% | -7.2 | -3.60% |
| 43 | 558 | 541 | 198.2 | 187 | 190 | 188 | 188.3 | 1.53 | 0.81% | -9.9 | -4.9% | | 189 | 187 | 189 | 188.3 | 1.15 | 0.6% | -9.9 | -4.95% |
| 44 | 558 | 541 | 198.2 | 190 | 191 | 189 | 190.0 | 1.00 | 0.00% | -8.2 | -4.1% | | 190 | 195 | 189 | 191.3 | 3.21 | 1.7% | -6.9 | -3.43% |
| 45 | 560 | 543 | 197.5 | 189 | 192 | 188 | 189.7 | 2.08 | 1.10% | -7.8 | -3.9% | | 191 | 191 | 191 | 191.0 | 0.00 | 0.0% | -6.5 | -3.24% |
| 46 | 561 | 544 | 197.1 | 190 | 188 | 189 | 189.0 | 1.00 | 0.53% | -8.1 | -4.1% | | 191 | 191 | 192 | 191.3 | 0.58 | 0.3% | -5.8 | -2.89% |
| 47 | 558 | 541 | 198.2 | 189 | 192 | 190 | 190.3 | 1.53 | 0.80% | -7.9 | -3.9% | | 193 | 192 | 192 | 192.3 | 0.58 | 0.3% | -5.9 | -2.93% |
| 48 | 558 | 541 | 198.2 | 191 | 189 | 191 | 190.3 | 1.15 | 0.61% | -7.9 | -3.9% | | 190 | 193 | 193 | 192.0 | 1.73 | 0.9% | -6.2 | -3.10% |
| 49 | 559 | 542 | 197.8 | 187 | 189 | 187 | 187.7 | 1.15 | 0.62% | -10.2 | -5.1% | | 192 | 192 | 193 | 192.3 | 0.58 | 0.3% | -5.5 | -2.75% |
| 50 | 555 | 538 | 199.3 | 195 | 190 | 190 | 191.7 | 2.89 | 1.51% | -7.6 | -3.8% | | 197 | 196 | 198 | 197.7 | 0.58 | 0.3% | -1.6 | -0.82% |
| Mean | 559.4 | 542.4 | 197.7 | | | Mean | 189.2 | 1.49 | 0.66% | -8.48 | -4.24% | Mean | | | Mean | 191.63 | 1.09 | 0.57% | -6.05 | -3.02% |
| Std Dev | 1.96 | 1.96 | 0.72 | | | Std Dev | 1.55 | 0.66 | 0.43% | -6.44 | -3.22% | High | | | Std Dev | 2.82 | 1.09 | 0.55% | 0.95 | 0.47% |
| % Std Dev | 0.35% | 0.36% | 0.36% | | | % Std Dev | 0.82% | 44.29% | 64.90% | -10.78 | -5.39% | Low | | | % Std Dev | 1.47% | 100.2% | 98.8% | -10.78 | -5.39% |

| Bag Number | Bag Weight (g) | Bag Adj Weight (Weight - 17 g) | Bag Adj Calculated Glucose (mg/dL) | Sample 1 (mg/dL) | Sample 2 (mg/dL) | Sample 3 (mg/dL) | Mean (mg/dL) | Std Dev (mg/dL) | % St Dev | Δ (Mean YSI - Bag Adj Glucose, mg/dL) | %Δ, Δ/(125 mg/dL) | Estimated %Δ, Δ/(200 mg/dL) |
|---|---|---|---|---|---|---|---|---|---|---|---|---|
| 1 | 561 | 544 | 123.2 | 116 | 116 | 115 | 115.7 | 0.58 | 0.50% | -7.5 | -6.0% | -3.76% |
| 2 | 558 | 541 | 123.9 | 117 | 115 | 115 | 115.7 | 1.15 | 1.00% | -8.2 | -6.6% | -4.11% |
| 3 | 560 | 543 | 123.4 | 114 | 115 | 114 | 114.3 | 0.58 | 0.50% | -9.1 | -7.3% | -4.54% |
| 4 | 560 | 543 | 123.4 | 116 | 116 | 116 | 116.0 | 0.00 | 0.00% | -7.4 | -5.9% | -3.71% |
| 5 | 559 | 542 | 123.6 | 116 | 117 | 117 | 116.7 | 0.58 | 0.49% | -7.0 | -5.6% | -3.49% |
| 6 | 557 | 540 | 124.1 | 116 | 117 | 115 | 116.0 | 1.00 | 0.86% | -8.1 | -6.5% | -4.05% |
| 7 | 555 | 538 | 124.6 | 116 | 117 | 116 | 116.3 | 0.58 | 0.50% | -8.2 | -6.6% | -4.12% |
| 8 | 560 | 543 | 123.4 | 116 | 116 | 115 | 115.7 | 0.58 | 0.50% | -7.8 | -6.2% | -3.88% |
| 9 | 560 | 543 | 123.4 | 116 | 117 | 115 | 116.0 | 1.00 | 0.86% | -7.4 | -5.9% | -3.71% |
| 10 | 559 | 542 | 123.6 | 117 | 118 | 117 | 117.3 | 0.58 | 0.49% | -6.3 | -5.1% | -3.16% |
| 11 | 557 | 540 | 124.1 | 117 | 118 | 118 | 117.7 | 0.58 | 0.49% | -6.4 | -5.2% | -3.22% |
| 12 | 562 | 545 | 123.0 | 115 | 115 | 115 | 115.0 | 0.00 | 0.00% | -8.0 | -6.4% | -3.98% |
| 13 | 560 | 543 | 123.4 | 117 | 118 | 117 | 117.3 | 0.58 | 0.49% | -6.1 | -4.9% | -3.04% |
| 14 | 559 | 542 | 123.6 | 117 | 117 | 117 | 117.0 | 0.00 | 0.00% | -6.6 | -5.3% | -3.32% |
| 15 | 559 | 542 | 123.6 | 114 | 118 | 115 | 115.7 | 2.08 | 1.80% | -8.0 | -6.4% | -3.99% |
| 16 | 562 | 545 | 123.0 | 116 | 113 | 115 | 114.7 | 1.53 | 1.33% | -8.3 | -6.6% | -4.15% |
| 17 | 557 | 540 | 124.1 | 114 | 117 | 117 | 116.0 | 1.73 | 1.49% | -8.1 | -6.5% | -4.05% |
| 18 | 560 | 543 | 123.4 | 119 | 120 | 119 | 119.3 | 0.58 | 0.48% | -4.1 | -3.3% | -2.04% |
| 19 | 560 | 543 | 123.4 | 119 | 118 | 118 | 118.3 | 0.58 | 0.49% | -5.1 | -4.1% | -2.54% |
| 20 | 559 | 542 | 123.6 | 121 | 121 | 121 | 121.0 | 0.00 | 0.00% | -2.6 | -2.1% | -1.32% |
| Mean | 559.2 | 542.2 | 123.6 | | | Mean | 116.6 | 0.71 | 0.6% | Mean | -7.0 | -5.6% | -3.51% |
| Std Dev | 1.74 | 1.69 | 0.39 | | | Std Dev | 1.6 | 0.57 | 0.5% | High | -2.6 | -2.1% | -1.32% |
| % Std Dev | 0.31% | 0.31% | 0.31% | | | % Std Dev | 1.4% | 79.8% | 80.2% | Low | -9.1 | -7.3% | -4.54% |

| Bag Number | Bag Weight (g) | Bag Adj Weight (Weight - 17 g) | Bag Adj Calculated Glucose (mg/dL) | Sample 1 (mg/dL) | Sample 2 (mg/dL) | Sample 3 (mg/dL) | Mean (mg/dL) | Std Dev (mg/dL) | % St Dev | Δ (Mean YSI - Bag Adj Glucose, mg/dL) | %Δ, Δ/(125 mg/dL) | Estimated %Δ, Δ/(200 mg/dL) |
|---|---|---|---|---|---|---|---|---|---|---|---|---|
| 21 | 558 | 541 | 123.9 | 123 | 123 | 123 | 123.0 | 0.00 | 0.00% | -0.9 | -0.7% | -0.44% |
| 22 | 559 | 542 | 123.6 | 126 | 126 | 124 | 125.3 | 1.15 | 0.92% | 1.7 | 1.3% | 0.84% |
| 23 | 557 | 540 | 124.1 | 122 | 125 | 124 | 123.7 | 1.53 | 1.24% | -0.4 | -0.4% | -0.22% |
| 24 | 558 | 541 | 123.9 | 122 | 122 | 122 | 122.0 | 0.00 | 0.00% | -1.9 | -1.5% | -0.94% |
| 25 | 559 | 542 | 123.6 | 121 | 120 | 118 | 119.7 | 1.53 | 1.28% | -4.0 | -3.2% | -1.99% |
| 26 | 559 | 542 | 123.6 | 123 | 126 | 125 | 124.7 | 1.53 | 1.23% | 1.0 | 0.8% | 0.51% |
| 27 | 556 | 539 | 124.3 | 125 | 126 | 126 | 125.7 | 0.58 | 0.46% | 1.3 | 1.1% | 0.66% |
| 28 | 559 | 542 | 123.6 | 125 | 124 | 122 | 123.7 | 1.53 | 1.24% | 0.0 | 0.0% | 0.01% |
| 29 | 559 | 542 | 123.6 | 124 | 123 | 123 | 123.3 | 0.58 | 0.47% | -0.3 | -0.3% | -0.16% |
| 30 | 557 | 540 | 124.1 | 125 | 125 | 126 | 125.3 | 0.58 | 0.46% | 1.2 | 1.0% | 0.61% |
| 31 | 557 | 540 | 124.1 | 123 | 124 | 121 | 122.7 | 1.53 | 1.25% | -1.4 | -1.2% | -0.72% |
| 32 | 557 | 540 | 124.1 | 126 | 126 | 125 | 125.7 | 0.58 | 0.46% | 1.6 | 1.2% | 0.78% |
| 33 | 557 | 540 | 124.1 | 131 | 131 | 130 | 130.7 | 0.58 | 0.44% | 6.6 | 5.2% | 3.28% |
| 34 | 559 | 542 | 123.6 | 125 | 124 | 121 | 123.3 | 2.08 | 1.69% | -0.3 | -0.3% | -0.16% |
| 35 | 558 | 541 | 123.9 | 128 | 127 | 127 | 127.3 | 0.58 | 0.45% | 3.5 | 2.8% | 1.73% |
| 36 | 556 | 539 | 124.3 | 131 | 128 | 127 | 128.7 | 2.08 | 1.62% | 4.3 | 3.5% | 2.16% |
| 37 | 557 | 540 | 124.1 | 123 | 123 | 125 | 123.7 | 1.15 | 0.93% | -0.4 | -0.4% | -0.22% |
| 38 | 564 | 547 | 122.5 | 125 | 125 | 125 | 125.0 | 0.00 | 0.00% | 2.5 | 2.0% | 1.24% |
| 39 | 560 | 543 | 123.4 | 124 | 123 | 124 | 123.7 | 0.58 | 0.47% | 0.2 | 0.2% | 0.12% |
| Mean | 558.2 | 541.2 | 123.8 | | | Mean | 124.6 | 0.96 | 0.8% | Mean | 0.7 | 0.6% | 0.37% |
| Std Dev | 1.81 | 1.76 | 0.40 | | | Std Dev | 2.5 | 0.67 | 0.5% | High | 6.6 | 5.2% | 3.28% |
| % Std Dev | 0.32% | 0.33% | 0.32% | | | % Std Dev | 2.0% | 69.7% | 69.9% | Low | -4.0 | -3.2% | -1.99% |

FIG. 21

| Syringe # | Weight 1 (g) | Weight 2 (g) | Weight 3 (g) | Mean (g) | Std Dev (g) | % Std Dev | | Δ (Mean - 1.5 g) | %Δ, Δ/(1.5 g) |
|---|---|---|---|---|---|---|---|---|---|
| 1 | 1.4646 | 1.4730 | 1.4747 | 1.4708 | 0.0054 | 0.37% | | -0.029 | -1.95% |
| 2 | 1.4745 | 1.4721 | 1.4758 | 1.4741 | 0.0019 | 0.13% | | -0.026 | -1.72% |
| 3 | 1.4713 | 1.4784 | 1.4818 | 1.4772 | 0.0054 | 0.36% | | -0.023 | -1.52% |
| 4 | 1.4811 | 1.4854 | 1.4862 | 1.4842 | 0.0027 | 0.18% | | -0.016 | -1.05% |
| 5 | 1.4874 | 1.4788 | 1.4769 | 1.4810 | 0.0056 | 0.38% | | -0.019 | -1.26% |
| 6 | 1.4711 | 1.4758 | 1.4694 | 1.4721 | 0.0033 | 0.23% | | -0.028 | -1.86% |
| 7 | 1.4447 | 1.4627 | 1.4653 | 1.4576 | 0.0112 | 0.77% | | -0.042 | -2.83% |
| 8 | 1.4722 | 1.4755 | 1.4765 | 1.4747 | 0.0023 | 0.15% | | -0.025 | -1.68% |
| 9 | 1.4844 | 1.4809 | 1.4820 | 1.4824 | 0.0018 | 0.12% | | -0.018 | -1.17% |
| 10 | 1.4897 | 1.4894 | 1.4906 | 1.4899 | 0.0006 | 0.04% | | -0.010 | -0.67% |
| 11 | 1.4713 | 1.4700 | 1.4819 | 1.4744 | 0.0065 | 0.44% | | -0.026 | -1.71% |
| 12 | 1.4527 | 1.4677 | 1.4728 | 1.4644 | 0.0104 | 0.71% | | -0.036 | -2.37% |
| 13 | 1.4423 | 1.4533 | 1.4641 | 1.4532 | 0.0109 | 0.75% | | -0.047 | -3.12% |
| 14 | 1.4684 | 1.4699 | 1.4603 | 1.4662 | 0.0052 | 0.35% | | -0.034 | -2.25% |
| 15 | 1.4589 | 1.4609 | 1.4565 | 1.4588 | 0.0022 | 0.15% | | -0.041 | -2.75% |
| 16 | 1.4647 | 1.4586 | 1.4652 | 1.4628 | 0.0037 | 0.25% | | -0.037 | -2.48% |
| 17 | 1.4864 | 1.4890 | 1.4863 | 1.4872 | 0.0015 | 0.10% | | -0.013 | -0.85% |
| 18 | 1.4728 | 1.4763 | 1.4740 | 1.4744 | 0.0018 | 0.12% | | -0.026 | -1.71% |
| 19 | 1.4864 | 1.4930 | 1.4925 | 1.4906 | 0.0037 | 0.25% | | -0.009 | -0.62% |
| 20 | 1.4777 | 1.4698 | 1.4742 | 1.4739 | 0.0040 | 0.27% | | -0.026 | -1.74% |
| | | | Mean | 1.4735 | 0.0045 | 0.31% | Mean | -0.026 | -1.77% |
| | | | Std Dev | 0.0107 | 0.0032 | 0.22% | High | -0.009 | -0.62% |
| | | | % Std Dev | 0.72% | 70.38% | 70.99% | Low | -0.047 | -3.12% |

FIG. 22

| Syringe # | Weight 1 (g) | Weight 2 (g) | Weight 3 (g) | Mean (g) | Std Dev (g) | % Std Dev | | Δ (Mean - 1.5 g) | %Δ, Δ/(1.5 g) |
|---|---|---|---|---|---|---|---|---|---|
| 21 | 1.4994 | 1.5013 | 1.4968 | 1.4992 | 0.0023 | 0.15% | | -0.001 | -0.06% |
| 22 | 1.4938 | 1.5080 | 1.5060 | 1.5026 | 0.0077 | 0.51% | | 0.003 | 0.17% |
| 23 | 1.4959 | 1.4997 | 1.4966 | 1.4974 | 0.0020 | 0.14% | | -0.003 | -0.17% |
| 24 | 1.4954 | 1.4946 | 1.4955 | 1.4952 | 0.0005 | 0.03% | | -0.005 | -0.32% |
| 25 | 1.4989 | 1.4965 | 1.4870 | 1.4941 | 0.0063 | 0.42% | | -0.006 | -0.39% |
| 26 | 1.4867 | 1.4987 | 1.4995 | 1.4950 | 0.0072 | 0.48% | | -0.005 | -0.34% |
| 27 | 1.5005 | 1.4949 | 1.4933 | 1.4962 | 0.0038 | 0.25% | | -0.004 | -0.25% |
| 28 | 1.4942 | 1.5108 | 1.5258 | 1.5103 | 0.0158 | 1.05% | | 0.010 | 0.68% |
| 29 | 1.4950 | 1.4934 | 1.4889 | 1.4924 | 0.0032 | 0.21% | | -0.008 | -0.50% |
| 30 | 1.4792 | 1.5043 | 1.4880 | 1.4905 | 0.0127 | 0.85% | | -0.009 | -0.63% |
| 31 | 1.4867 | 1.4930 | 1.4945 | 1.4914 | 0.0041 | 0.28% | | -0.009 | -0.57% |
| 32 | 1.4944 | 1.5057 | 1.5103 | 1.5035 | 0.0082 | 0.54% | | 0.003 | 0.23% |
| 33 | 1.5126 | 1.4935 | 1.5009 | 1.5023 | 0.0096 | 0.64% | | 0.002 | 0.16% |
| 34 | 1.4779 | 1.4940 | 1.4961 | 1.4893 | 0.0100 | 0.67% | | -0.011 | -0.71% |
| 35 | 1.5082 | 1.5046 | 1.5033 | 1.5054 | 0.0025 | 0.17% | | 0.005 | 0.36% |
| 36 | 1.5037 | 1.4970 | 1.5009 | 1.5005 | 0.0034 | 0.22% | | 0.001 | 0.04% |
| 37 | 1.4641 | 1.4692 | 1.4590 | 1.4641 | 0.0051 | 0.35% | | -0.036 | -2.39% |
| 38 | 1.5094 | 1.5037 | 1.5066 | 1.5066 | 0.0029 | 0.19% | | 0.007 | 0.44% |
| 39 | 1.5133 | 1.5067 | 1.5070 | 1.5090 | 0.0037 | 0.25% | | 0.009 | 0.60% |
| | | | Mean | 1.4971 | 0.0058 | 0.39% | Mean | -0.003 | -0.19% |
| | | | Std Dev | 0.0101 | 0.0040 | 0.27% | High | 0.010 | 0.68% |
| | | | % Std Dev | 0.68% | 68.81% | 68.60% | Low | -0.036 | -2.39% |

FIG. 23

CALIBRANT INFUSION FLUID SOURCE PREPARATION

CROSS-REFERENCE TO RELATED APPLICATIONS

This application claims the benefit of U.S. Provisional Application No. 61/222,425, filed Jul. 1, 2009, which is incorporated by reference in its entirety.

BACKGROUND

Technical Field

In general, embodiments herein disclosed relate to analyte measuring systems and, more specifically, methods and systems for calibrant infusion fluid source preparation.

Controlling blood glucose levels for diabetics and other patients can be a vital component in critical care, particularly in an intensive care unit (ICU), operating room (OR), or emergency room (ER) setting where time and accuracy are essential. Presently, one of the most common ways to obtain a highly accurate blood glucose measurement from a patient is by a direct time-point method, which is an invasive method that involves drawing a blood sample and sending it off for laboratory analysis. This is a time-consuming method that is often incapable of producing needed results in a timely manner. Other minimally invasive methods such as subcutaneous methods involve the use of a lancet or pin to pierce the skin to obtain a small sample of blood, which is then smeared on a test strip and analyzed by a glucose meter. While these minimally invasive methods may be effective in determining trends in blood glucose concentration, they generally do not track glucose accurately enough to be used for intensive insulin therapy, for example, where inaccuracy at conditions of hypoglycemia could pose a very high risk to the patient.

Electro-chemical biosensors have been developed for measuring various analytes in a substance, such as glucose. An analyte is a substance or chemical constituent that is determined in an analytical procedure, such as a titration. For instance, in an immunoassay, the analyte may be the ligand or the binder, where in blood glucose testing, the analyte is glucose. Electro-chemical biosensors comprise electrolytic cells including electrodes used to measure an analyte. Two types of electro-chemical biosensors are potentiometric and amperometric biosensors.

Amperometric biosensors, for example, are known in the medical industry for analyzing blood chemistry. These types of sensors contain enzyme electrodes, which typically include an oxidase enzyme, such as glucose oxidase, that is immobilized within a membrane on the surface of an electrode. In the presence of blood, the membrane selectively passes an analyte of interest, e.g. glucose, to the oxidase enzyme where it undergoes oxidation or reduction, e.g. the reduction of oxygen to hydrogen peroxide. Amperometric biosensors function by producing an electric current when a potential sufficient to sustain the reaction is applied between two electrodes in the presence of the reactants. For example, in the reaction of glucose and glucose oxidase, the hydrogen peroxide reaction product may be subsequently oxidized by electron transfer to an electrode. The resulting flow of electrical current in the electrode is indicative of the concentration of the analyte of interest.

An intravenous blood glucose (IVBG) sensor system uses a heparinized saline solution injected with a dextrose solution to provide a fixed glucose concentration for sensor flush and calibration. The IVBG sensor relies on an accurate, consistent glucose concentration in the heparinized calibrant infusion fluid source in order to calibrate the sensor. Therefore, the accuracy and consistency of the glucose concentration is of utmost importance.

There are several known methods possible to prepare the calibrant infusion fluid source, also referred to herein as the calibrant bag. However, each of the known methods present problems related thereto. In one method, referred to as the premixed option, an IV bag is filled with saline and the selected amount of glucose at the IV bag supplier's location. Although this is highly convenient option, it presents the problem of accurately measuring the glucose concentration in the bag immediately prior to use. The pre-mixed option may require measuring the glucose concentration immediately prior to use.

Additionally, since the IVBG sensor system is intended for use in a hospital setting, such as the Intensive Care Unit (ICU), Operating Room (OR), step down ward or the like, commonly used glucose analyzers used in the hospital are candidate instruments to measure the glucose concentration in the premixed bag immediately prior to use. Unfortunately, these glucose analyzers are designed for use with whole blood and/or blood plasma and not a saline based glucose solution. Therefore, the premixed option is not viable because currently available glucose analyzers used in the hospital environment are incapable of accurately measuring the glucose concentration in a saline-based glucose solution.

In another method, referred to as the injection option, glucose is injected in the saline filled IV bag immediately prior to use and the glucose concentration of the contents of the bag is verified. However, this option poses the same problem as the premixed option; accurately measuring the glucose concentration, since the same glucose analyzers discussed above are relied upon and may not be capable of accurately measuring the glucose concentration in a saline solution.

Therefore, a need exists to develop methods and systems for preparing calibrant infusion fluid source to insure consistent and/or accurate concentration of the glucose in the calibrant infusion fluid sources.

SUMMARY

The following presents a simplified summary of one or more embodiments in order to provide a basic understanding of such embodiments. This summary is not an extensive overview of all contemplated embodiments, and is intended to neither identify key or critical elements of all embodiments, nor delineate the scope of any or all embodiments. Its sole purpose is to present some concepts of one or more embodiments in a simplified form as a prelude to the more detailed description that is presented later.

Methods and systems are defined for preparation of calibrant infusion fluid sources. In one embodiment, a precise volume of glucose is injected into a saline-solution filled calibrant infusion fluid source proximate in time to conducting a calibration procedure. The glucose concentration in the calibrant infusion fluid source is subsequently calculated based on the measured weight of the saline-solution, as determined prior to glucose injection, and the volume of glucose injected. This method provides a highly accurate and convenient manner for use in a hospital environment. In another embodiment, a premixed calibrant infusion fluid source is provided that includes saline solution and a predetermined concentration of glucose. In such embodiments, shelf life problems related to water evaporation are mitigated by hermetically covering or otherwise hermetically containing the calibrant infusion fluid source up until the point of use. This procedure ensures that the glucose concentration in the calibrant infusion fluid source is consistent with the concentration at the time of premix.

According to one embodiment of the invention, a method for preparing a calibrant infusion fluid source is defined. The method includes providing a calibrant infusion fluid source that includes a saline solution and determining content weight in the calibrant infusion fluid source. The method further includes adding a predetermined volume of a predetermined glucose concentrate into the calibrant infusion fluid source and determining a concentration of glucose in the calibrant infusion fluid source based on the content weight in the calibrant infusion fluid source and the predetermined volume of the predetermined glucose concentrate. Further, according to the method, a calibration procedure ensues proximate in time to adding the predetermined volume of the predetermined glucose concentrate into the calibrant infusion fluid source.

According to specific embodiments of the method, providing the calibrant infusion fluid source may further include providing the calibrant infusion fluid source that includes the saline solution and an anti-clotting agent, such as heparin or the like. In one such specific embodiment, providing the calibrant infusion fluid source that includes the saline solution and heparin further includes providing the calibrant infusion fluid source that includes about 1000 units of heparin in a 500 mL volume of 0.9 percent by weight (% wt) sodium chloride (NaCl).

According to other specific embodiments of the method, determining content weight in the calibrant infusion fluid source further includes weighing the calibrant infusion fluid source and subtracting an empty calibrant infusion fluid source weight from the weight of the calibrant infusion fluid source.

In yet further specific embodiments of the method, adding the predetermined volume further comprises injecting the predetermined volume of the predetermined glucose concentrate into the calibrant infusion fluid source. In such embodiments of the method, injecting the predetermined volume may further include injecting the predetermined volume of the predetermined glucose concentrate using a syringe having a volume-controlling mechanism, such as a dimpled stop, a tapered barrel, or the like. In still further embodiments of the method, injecting the predetermined volume may further include injecting the predetermined volume of the predetermined glucose concentrate using a previously un-used syringe and wherein the injection is a single injection of the syringe absent a flush.

A system for preparing a calibrant infusion fluid source provides for another embodiment of the invention. The system includes a calibrant infusion fluid source including a saline solution and a weighing device operable to determine a weight of the calibrant infusion fluid source. The system additionally includes a syringe operable to inject a predetermined volume of a predetermined glucose concentrate into the calibrant infusion fluid source and a calculation device operable to calculate a concentration of glucose in the calibrant infusion fluid source based on a content weight in the calibrant infusion fluid source and the predetermined volume of the predetermined glucose concentrate. In addition, the system dictates that an intravenous blood glucose calibration procedure ensues proximate in time to injecting the predetermined volume of the predetermined glucose concentrate into the calibrant infusion fluid source.

In one specific embodiment of the system, the calibrant infusion fluid source further includes the saline solution and an anti-clotting agent, such as heparin or the like. As such, in one specific embodiment of the system, the calibrant infusion fluid source includes about 1000 units of heparin in a 500 mL volume of 0.9 percent by weight sodium chloride (NaCl).

In another specific embodiment of the system, the calculation device if further operable to determine the content weight in the calibrant infusion fluid source by subtracting an empty calibrant infusion fluid source weight from the weight of the calibrant infusion fluid source including the saline solution.

In other specific embodiments of the system, the syringe further includes a volume-controlling mechanism, such as a dimpled stop, a tapered barrel, or the like. In another specific embodiment of the system, the syringe is further defined as a previously un-used syringe.

Another method for preparing a calibrant infusion fluid source defines a still further embodiment of the invention. The method includes providing a calibrant infusion fluid source that includes a saline solution and a predetermined concentration of glucose, applying a hermetic containment to the calibrant infusion fluid source, and removing the hermetic containment proximate in time to conducting an intravenous blood glucose calibration procedure.

In one specific embodiment of the method, providing the calibrant infusion fluid source further includes providing the calibrant infusion fluid source that includes the saline solution, the predetermined concentration of glucose and an anti-clotting agent, such as heparin or the like.

In another specific embodiment of the method, applying a hermetic containment further includes wrapping the calibrant infusion fluid source in a hermetic material, such metalized plastic, a metal foil or the like. In a still further specific embodiment of the method, applying a hermetic containment further includes placing the calibrant infusion fluid source in a metalized bag and, additionally, heat-sealing the metalized bag after placing the calibrant infusion fluid source in the metalized bag.

Another system for preparing a calibrant infusion fluid source provides yet another embodiment of the invention. The system includes a calibrant infusion fluid source including a saline solution and a predetermined concentration of glucose. The system additionally includes a hermetic containment surrounding the calibrant infusion fluid source that is operable to be removed proximate in time to conducting an intravenous blood glucose calibration procedure.

According to specific embodiments of the system, the calibrant infusion fluid source further includes the saline solution, the predetermined concentration of glucose and an anti-clotting agent, such as heparin or the like.

In other specific embodiments of the system, the hermetic containment further includes a hermetic wrap, such as metalized plastic, a metal foil or the like, surrounding the calibrant infusion fluid source. In yet another specific embodiment of the system, the hermetic containment is further defined as a metalized bag, which may additionally include a heat-sealable seal.

To the accomplishment of the foregoing and related ends, the one or more embodiments comprise the features hereinafter fully described and particularly pointed out in the claims. The following description and the annexed drawings set forth in detail certain illustrative features of the one or more embodiments. These features are indicative, however, of but a few of the various ways in which the principles of various embodiments may be employed, and this description is intended to include all such embodiments and their equivalents.

BRIEF DESCRIPTION OF THE DRAWINGS

Figure 1:
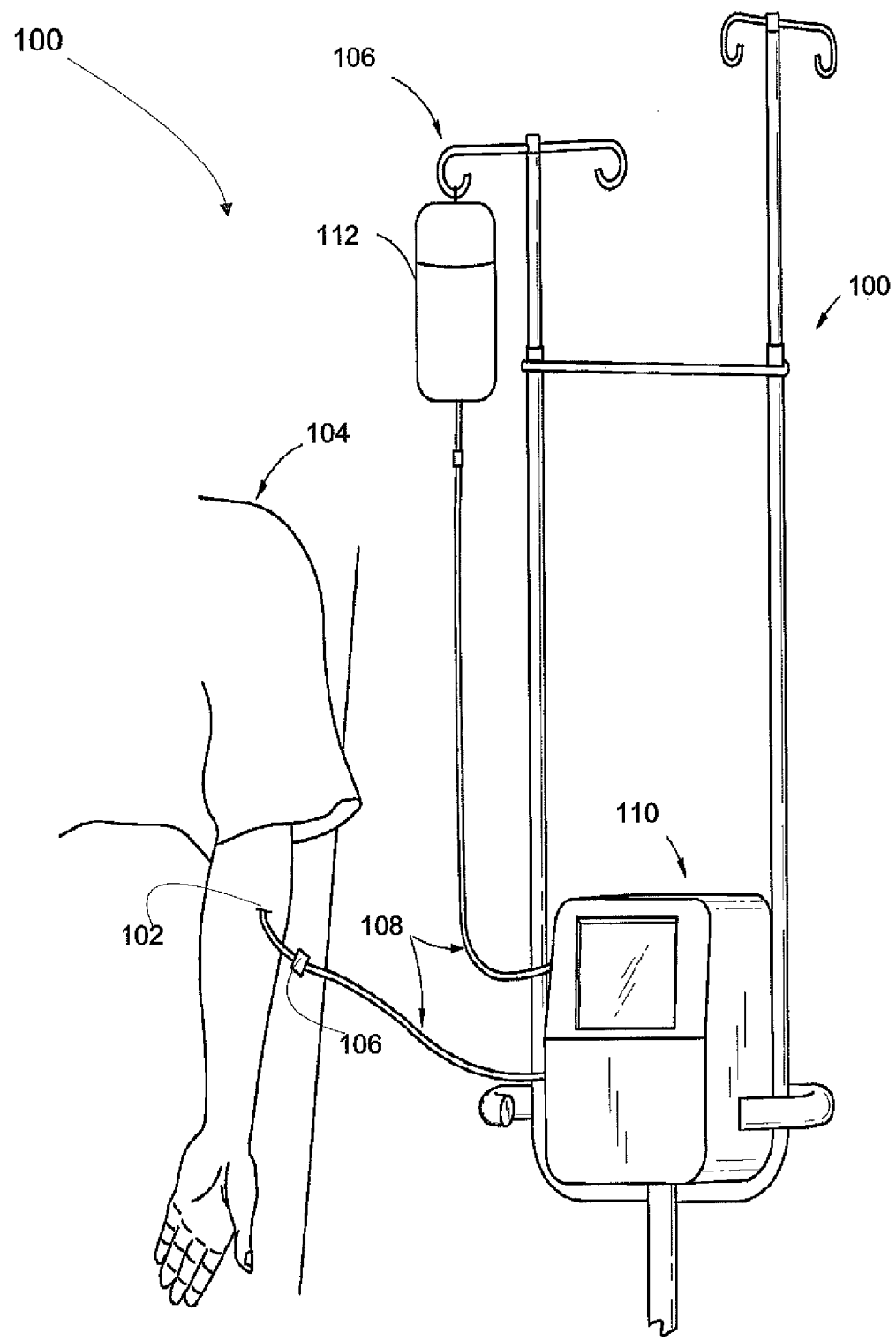
Figure 2:
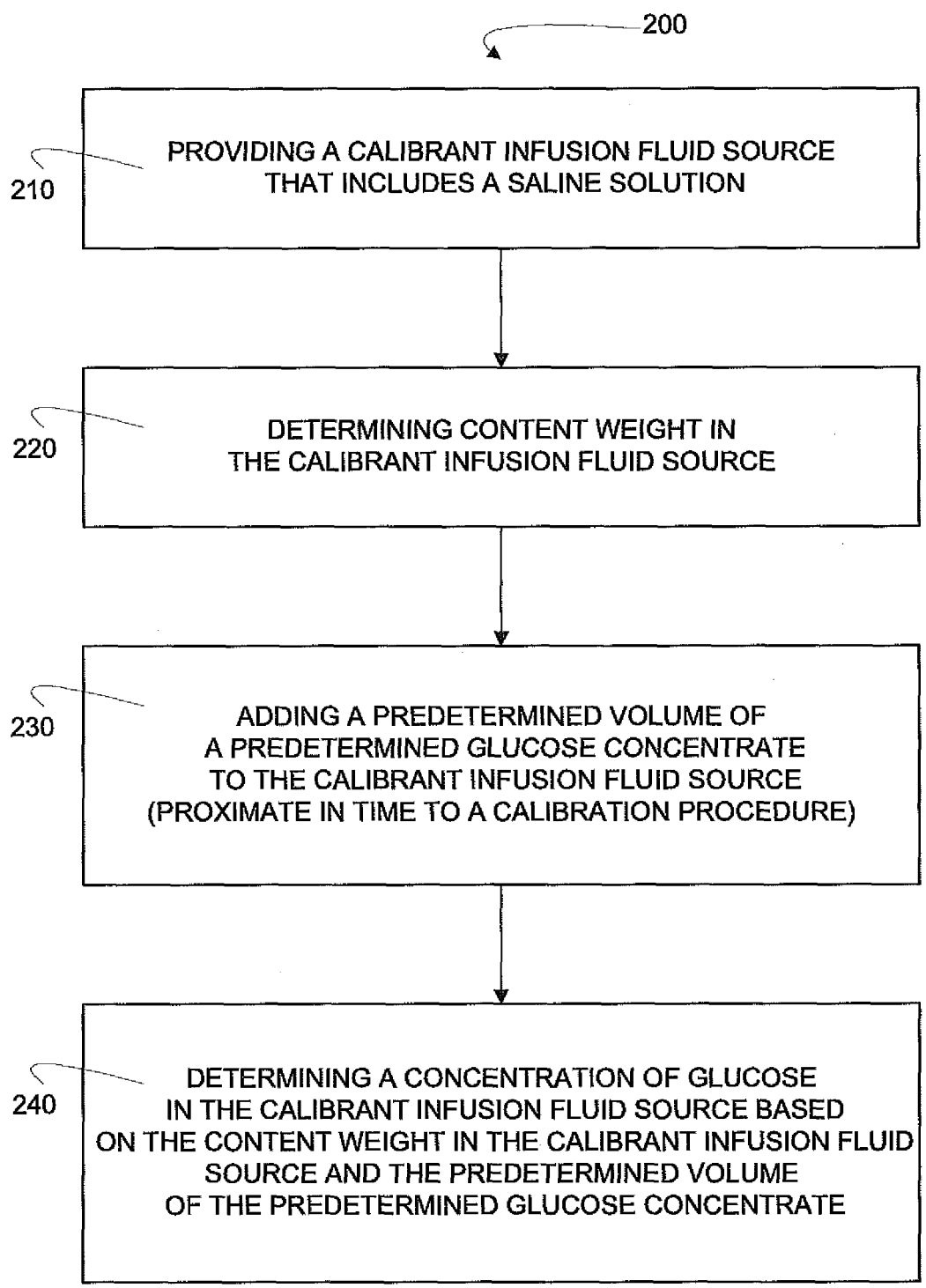
Figure 3:
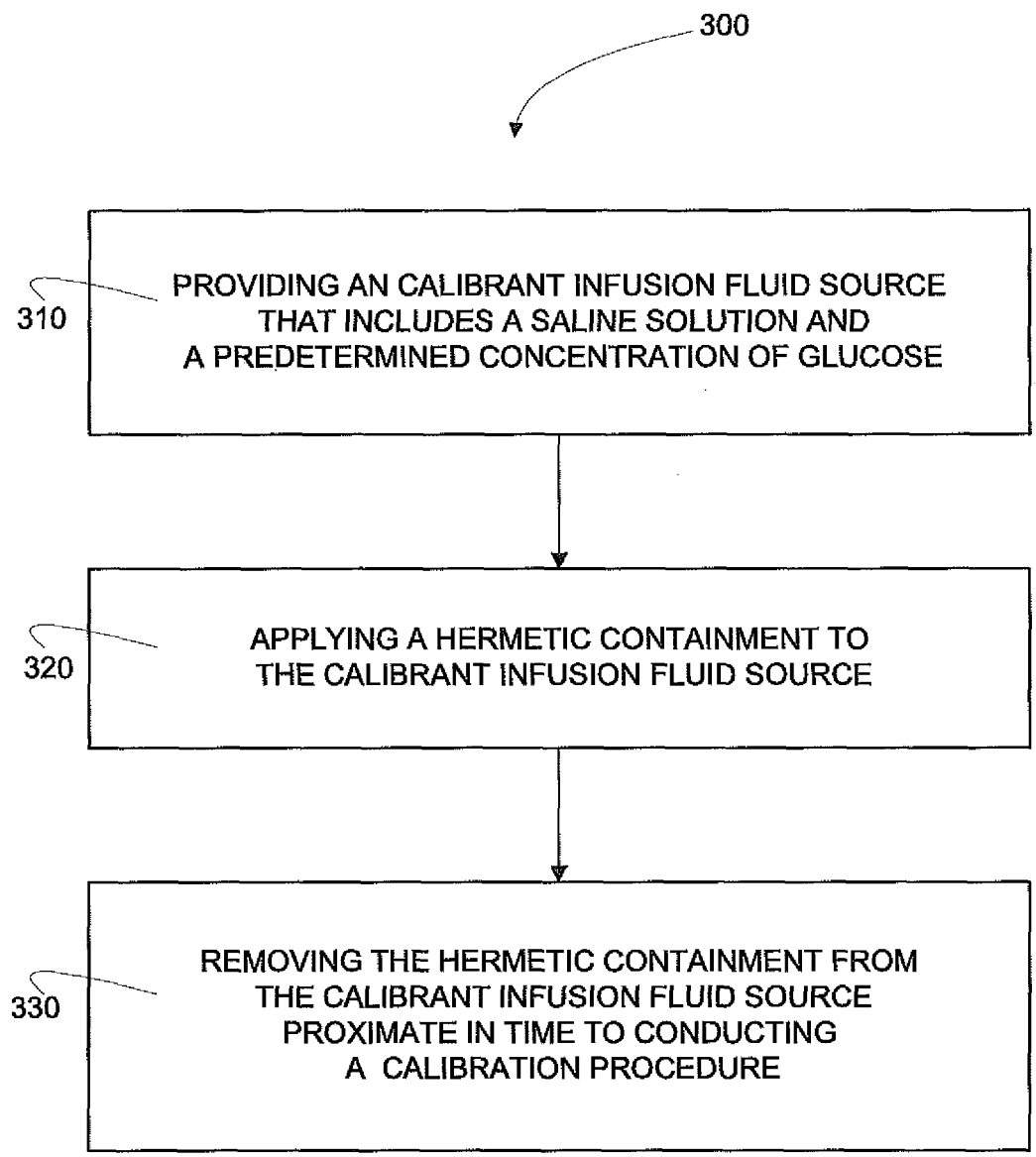
Figure 4:
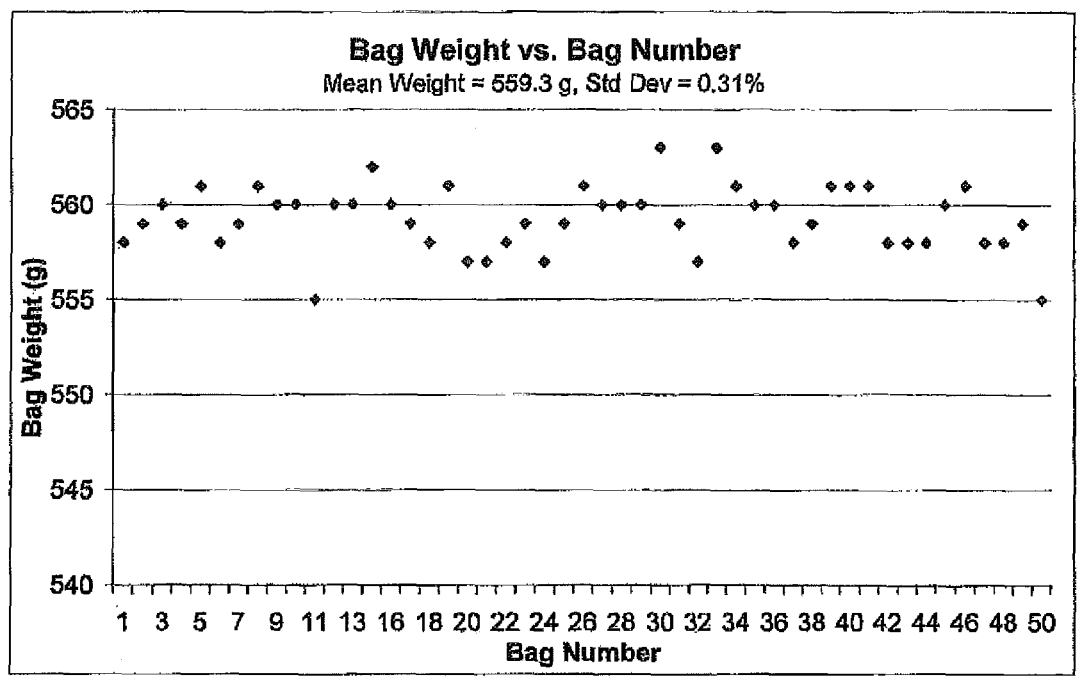
Figure 5:
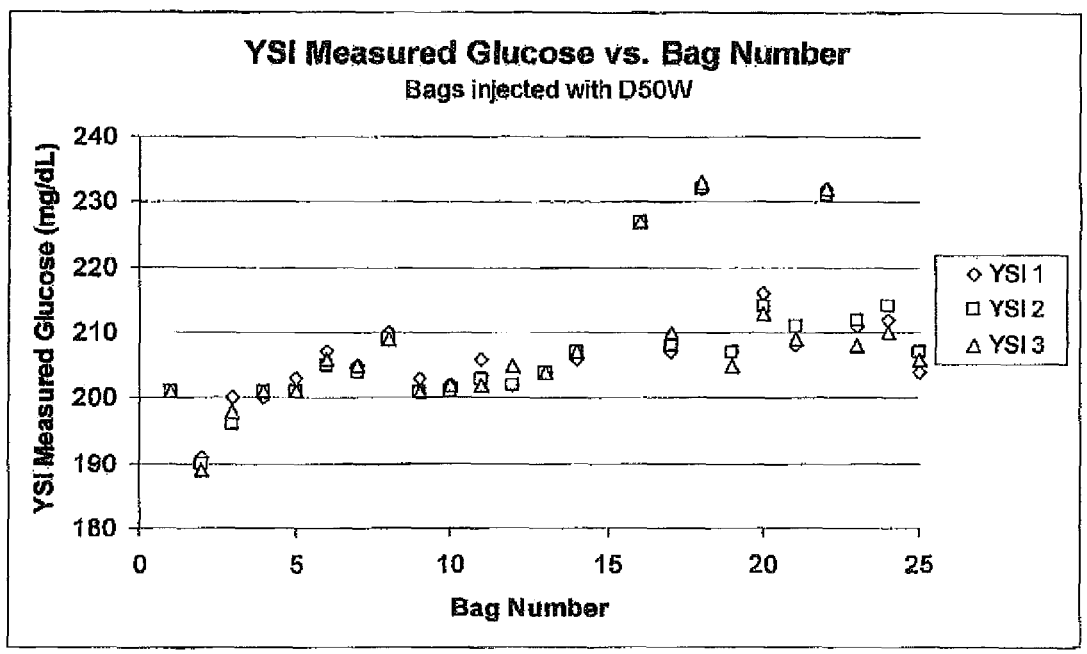
Figure 6:
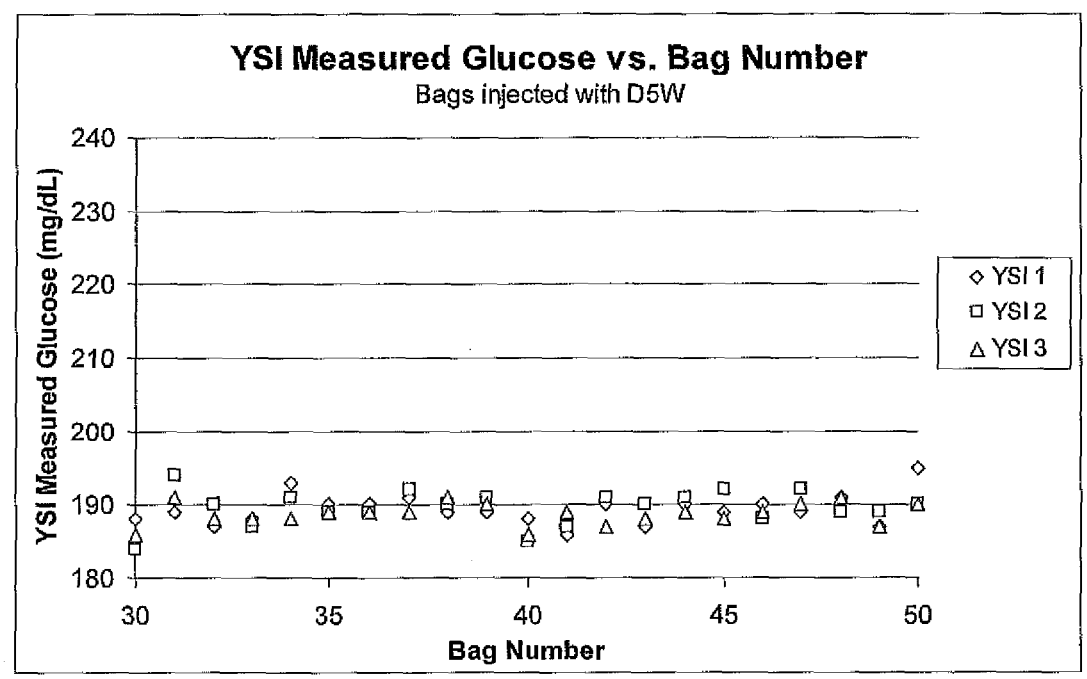
Figure 7:
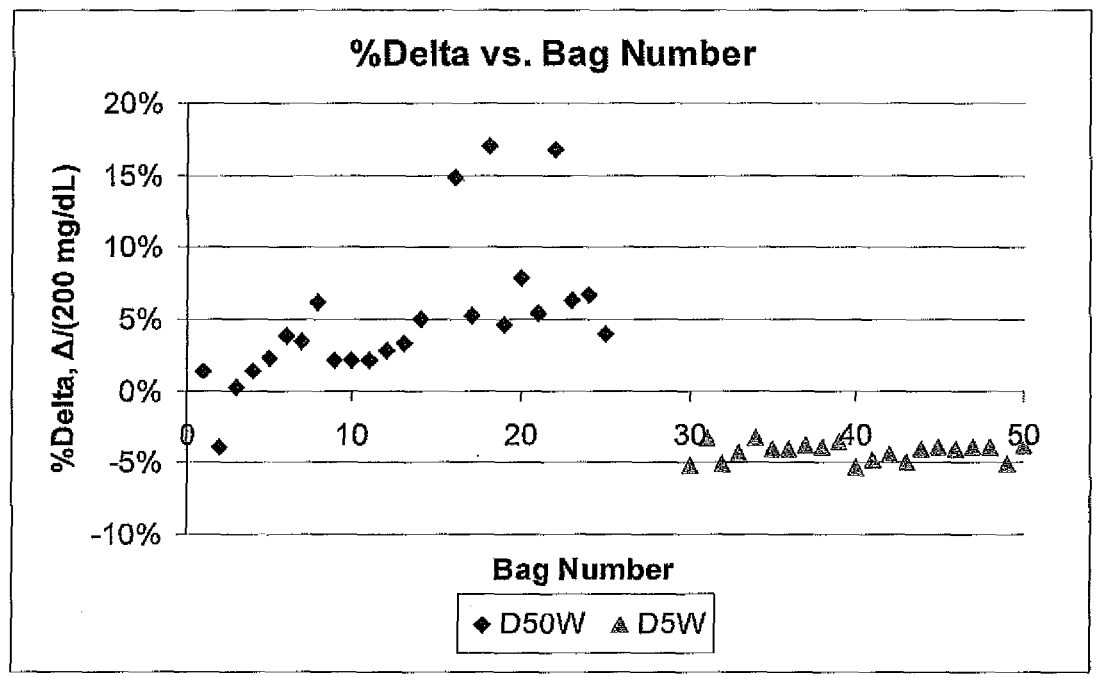
Figure 10:
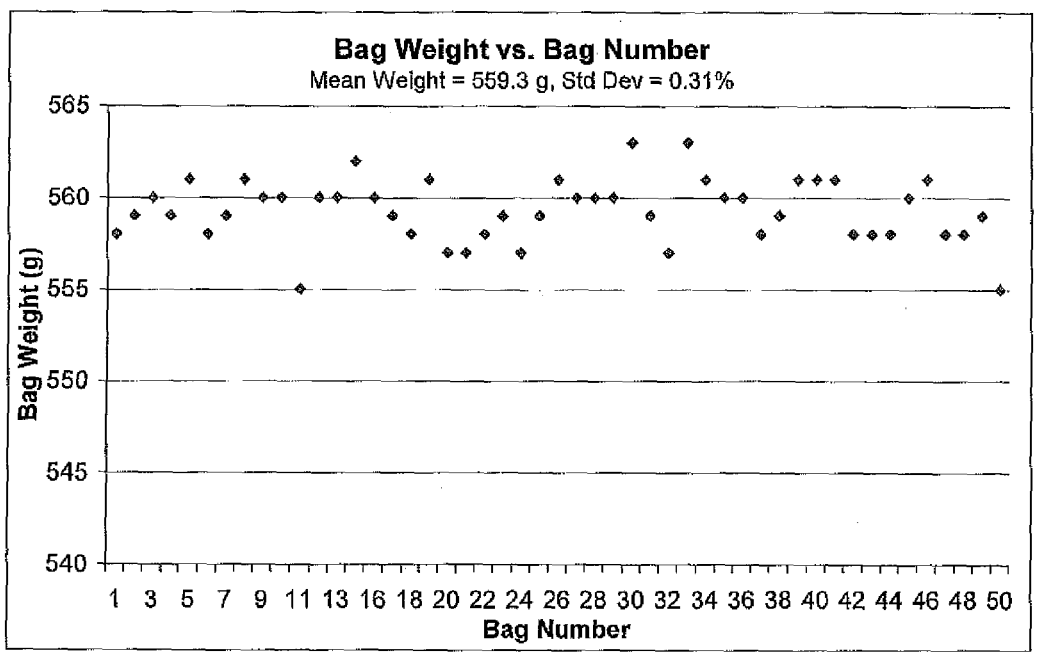
Figure 11:
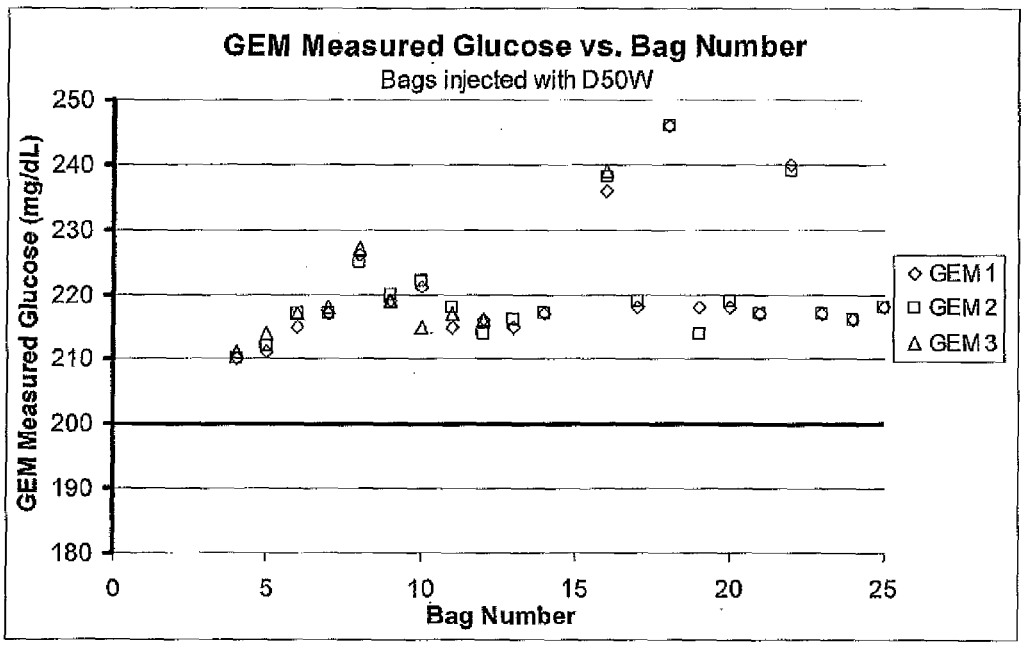
Figure 12:
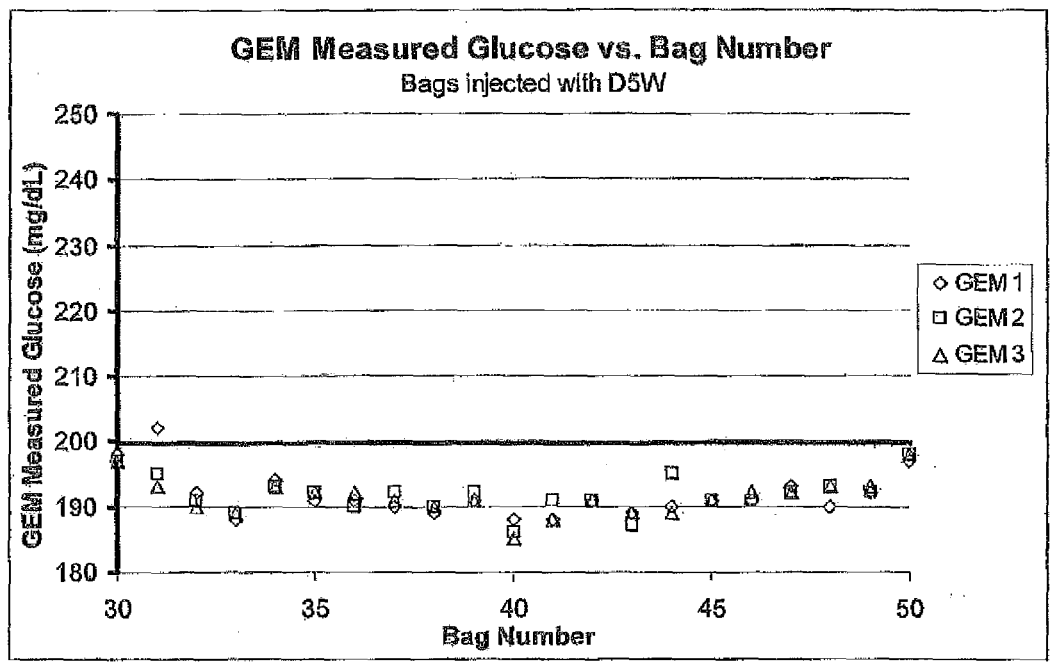
Figure 13:
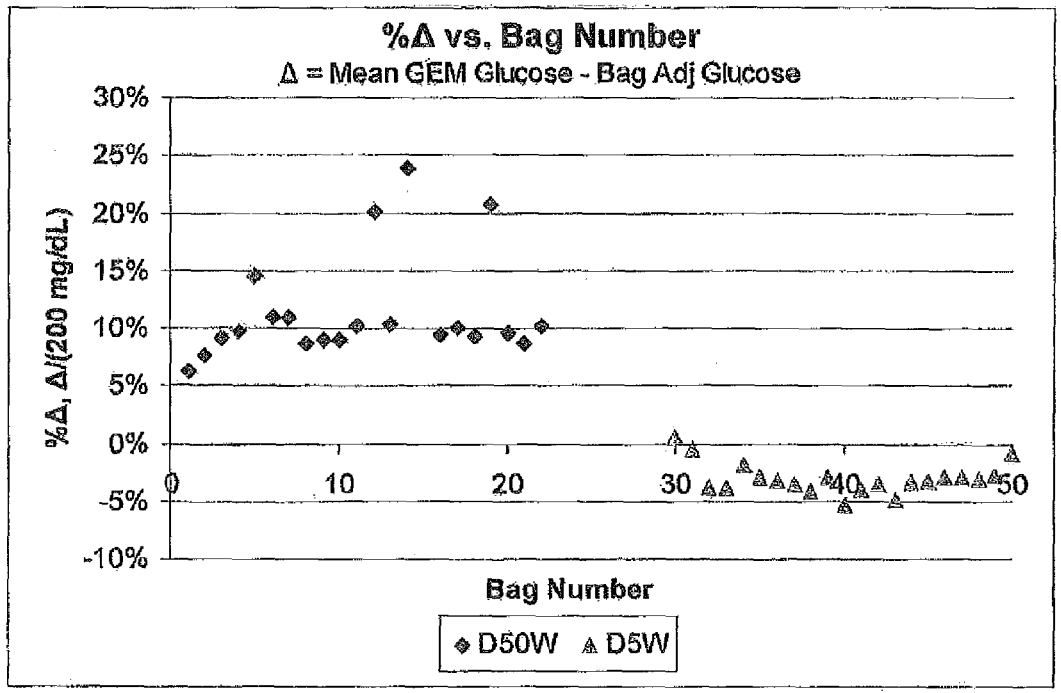
Figure 16:
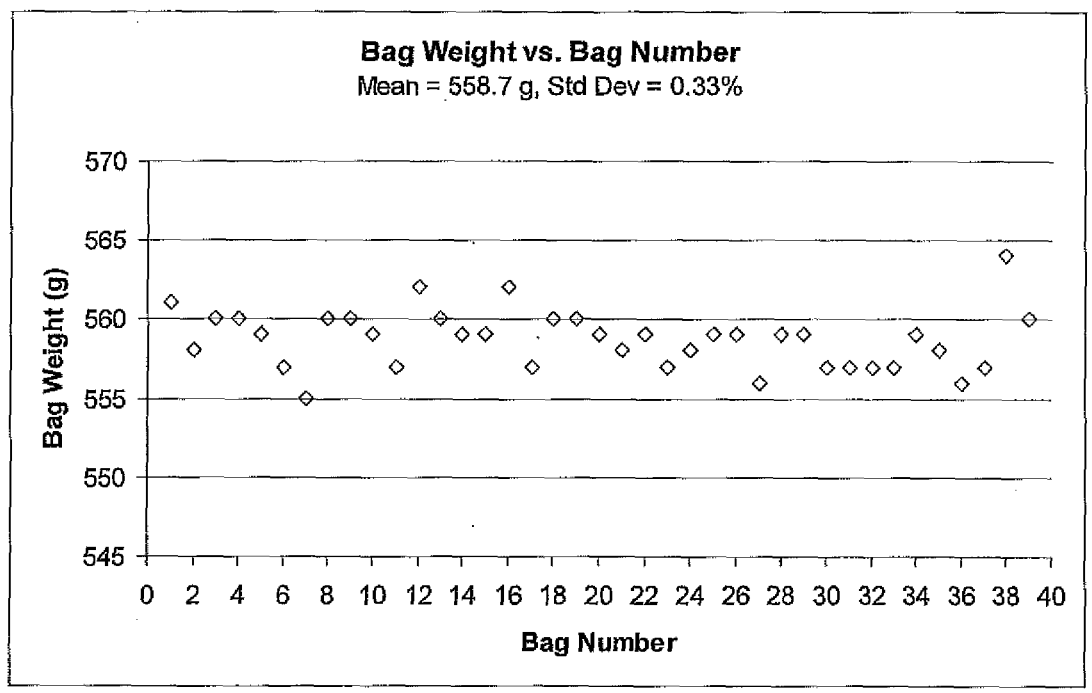
Figure 17:
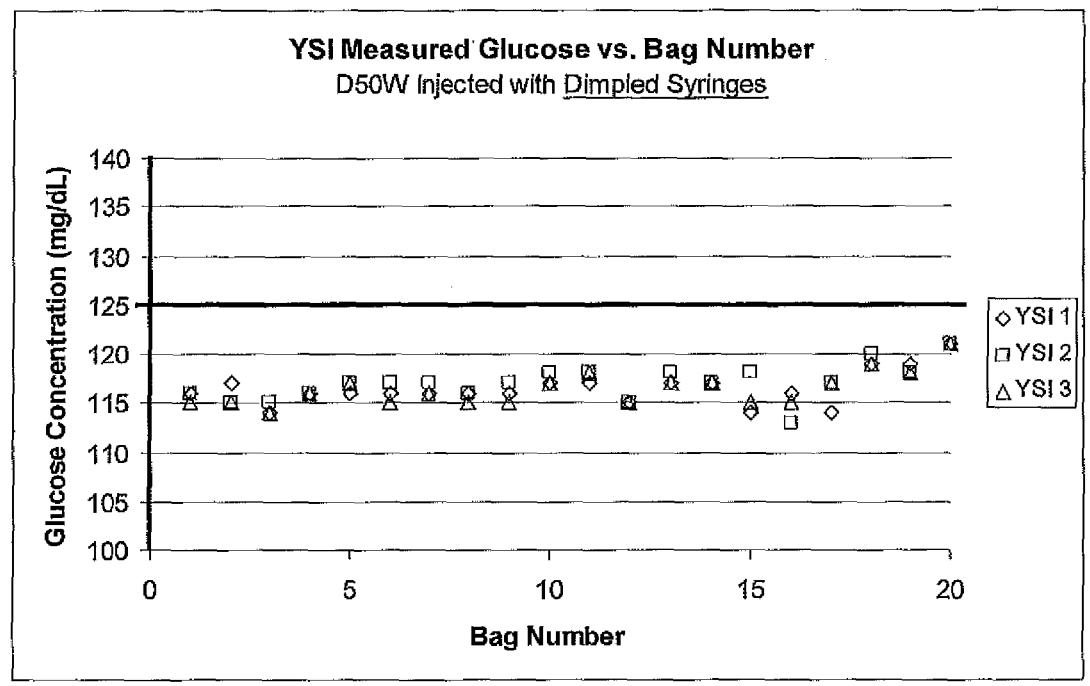
Figure 18:
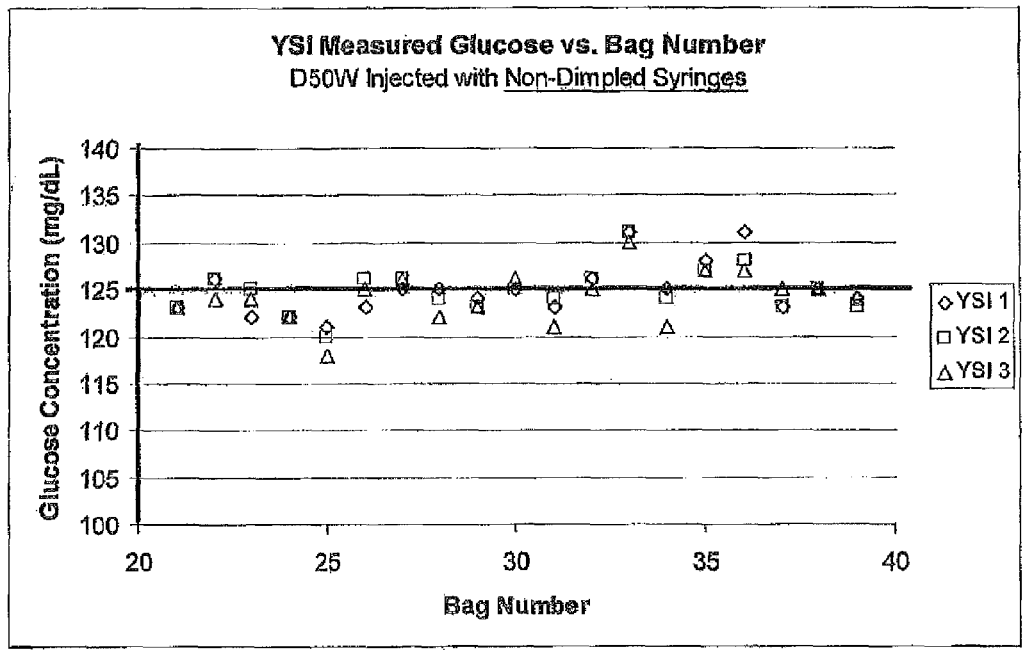
Figure 19:
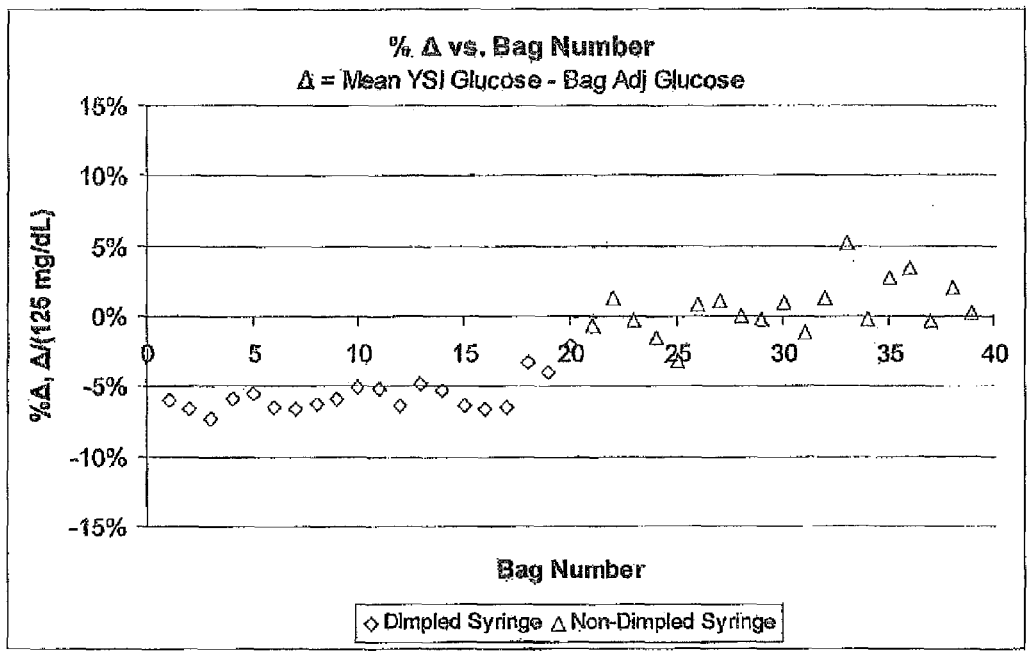
Figure 24:
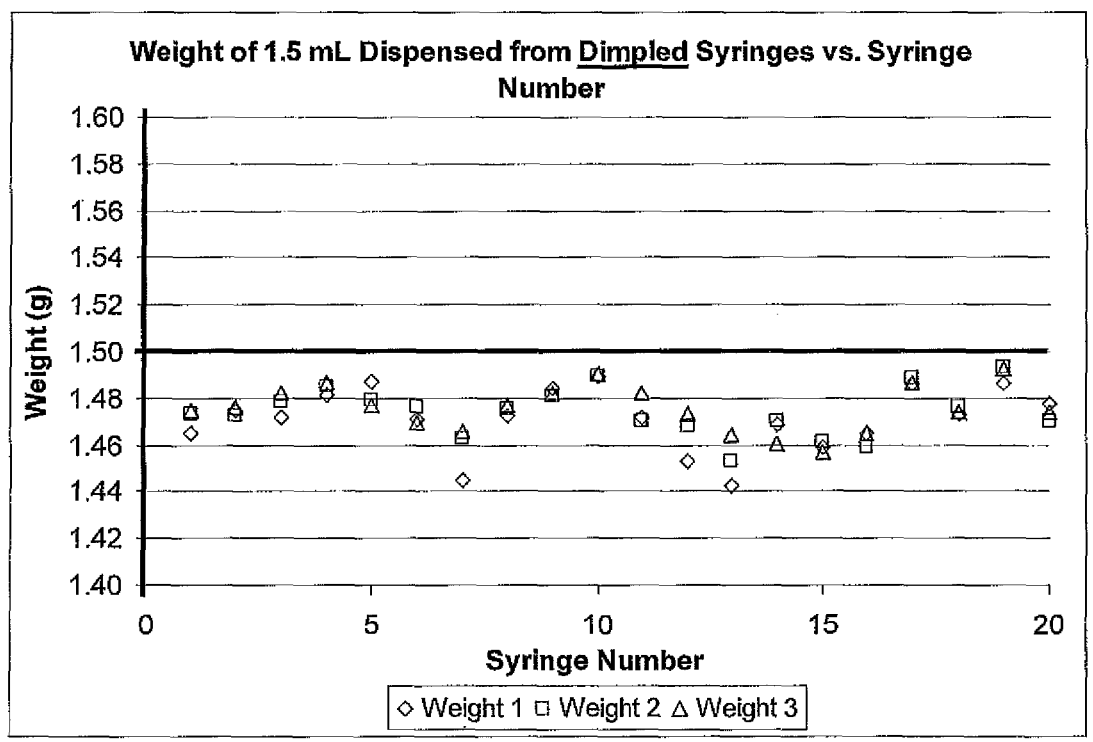
Figure 25:
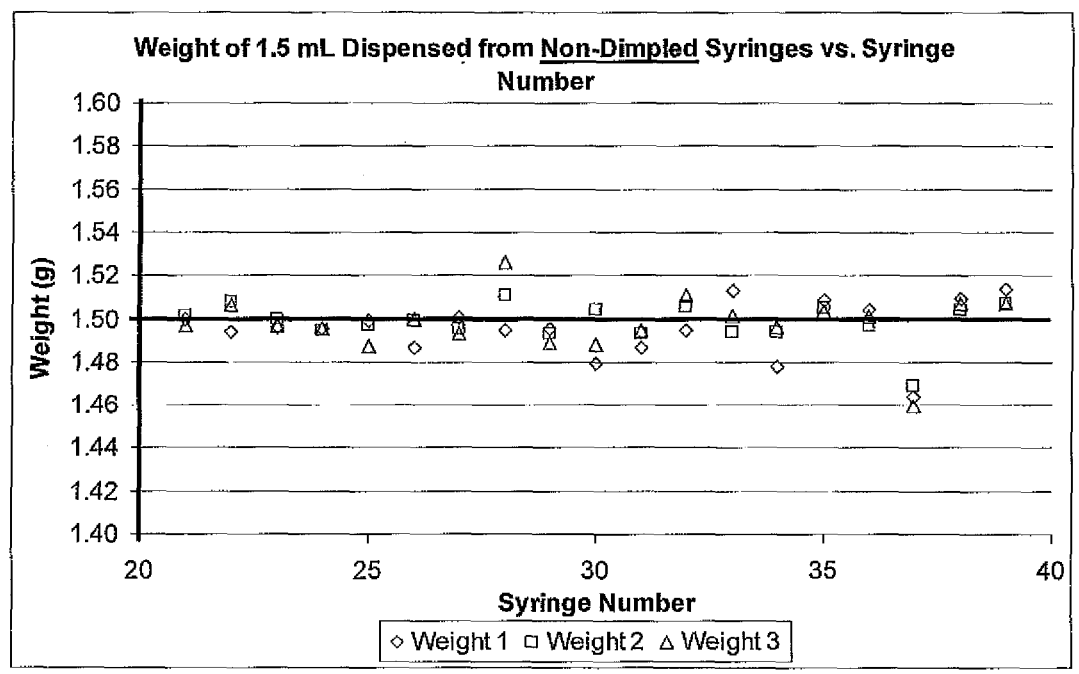
Figure 26:
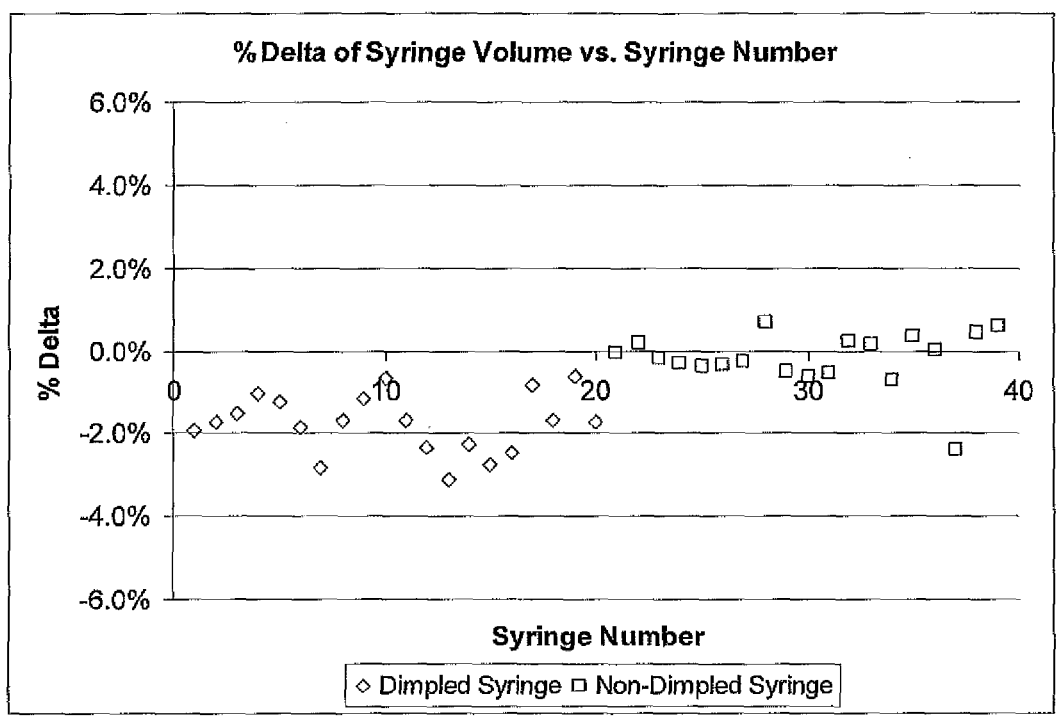

Having thus described embodiments of the invention in general terms, reference will now be made to the accompanying drawings, which are not necessarily drawn to scale, and wherein:

FIG. 1 is a schematic diagram of a system for blood glucose monitoring, according to an embodiment of the present invention;

FIG. 2 is a flow diagram of a method for preparation of a calibrant infusion fluid source, in accordance with an embodiment of the present invention;

FIG. 3 is a flow diagram of a method for preparation of a calibrant infusion fluid source, in accordance with present embodiments;

FIG. 4 is a graphical representation of calibrant infusion fluid source weight versus calibrant infusion fluid source identifier, in accordance with present embodiments;

FIG. 5 is a graphical representation of triplicate YSI glucose measurements for 50% dextrose-injected calibrant infusion fluid source, in accordance with present embodiments;

FIG. 6 is a graphical representation of triplicate YSI glucose measurements for 5% dextrose-injected calibrant infusion fluid source, in accordance with an embodiment of the present invention;

FIG. 7 is a graphical representation of percentage delta glucose for YSI measurements versus calibrant infusion fluid source identifier, in accordance with yet another embodiment of the present invention;

FIG. 8 is a table of collected data for 50% dextrose calibrant infusion fluid sources, in accordance with yet another embodiment of the present invention;

FIG. 9 is a table of collected data for 5% dextrose injected calibrant infusion fluid sources, in accordance with yet another embodiment of the present invention;

FIG. 10 is a graphical representation of calibrant infusion fluid source weight versus calibrant infusion fluid source identifier, in accordance with present embodiments;

FIG. 11 is a graphical representation of triplicate GEM glucose measurements for 50% dextrose-calibrant infusion fluid sources, in accordance with yet another embodiment of the present invention;

FIG. 12 is a graphical representation of triplicate YSI glucose measurements for 5% dextrose-injected calibrant infusion fluid sources, in accordance with yet another embodiment of the present invention;

FIG. 13 is a graphical representation of percentage delta glucose for GEM measurements versus calibrant infusion fluid source identifier, in accordance with yet another embodiment of the present invention;

FIG. 14 is a table of collected data for 50% dextrose injected calibrant infusion fluid sources, in accordance with yet another embodiment of the present invention;

FIG. 15 is a table of collected data for 5% dextrose injected calibrant infusion fluid sources, in accordance with yet another embodiment of the present invention;

FIG. 16 is a graphical representation of calibrant infusion fluid source weight versus calibrant infusion fluid source identifier, in accordance with yet another embodiment of the present invention;

FIG. 17 is a graphical representation of YSI measured glucose in calibrant infusion fluid sources injected with dimpled syringes versus calibrant infusion fluid source identifier, in accordance with yet another embodiment of the present invention;

FIG. 18 is a graphical representation of YSI measured glucose in calibrant infusion fluid sources injected with non-dimpled syringes versus calibrant infusion fluid source identifier, in accordance with yet another embodiment of the present invention;

FIG. 19 is a graphical representation of percentage delta glucose for YSI measurements in dimpled and non-dimpled syringe injections versus calibrant infusion fluid source identifier, in accordance with yet another embodiment of the present invention;

FIG. 20 is a table of collected data for dimpled syringe-injected calibrant infusion fluid sources, in accordance with yet another embodiment of the present invention;

FIG. 21 is a table of collected data for non-dimpled syringe-injected calibrant infusion fluid sources, in accordance with yet another embodiment of the present invention;

FIG. 22 is a table of collected data for volume weight analysis of dimpled syringe-injected calibrant infusion fluid sources, in accordance with yet another embodiment of the present invention;

FIG. 23 is a table of collected data for volume weight analysis of non-dimpled syringe-injected calibrant infusion fluid sources, in accordance with yet another embodiment of the present invention;

FIG. 24 is a graphical representation of triplicate weight measurements for 1.5 mL volume glucose injections using a dimpled syringe versus syringe identifier, in accordance with yet another embodiment of the present invention;

FIG. 25 is a graphical representation of triplicate weight measurements for 1.5 mL volume glucose injections using a non-dimpled syringe versus syringe identifier, in accordance with yet another embodiment of the present invention; and FIG. 26 is a graphical representation of percentage delta of syringe volume versus syringe number, in accordance with yet another embodiment of the present invention.

DETAILED DESCRIPTION OF EMBODIMENTS OF THE INVENTION

Embodiments of the present invention will now be described more fully hereinafter with reference to the accompanying drawings, in which some, but not all, embodiments of the invention are shown. Indeed, the invention may be embodied in many different forms and should not be construed as limited to the embodiments set forth herein; rather, these embodiments are provided so that this disclosure will satisfy applicable legal requirements. In the following description, for purposes of explanation, numerous specific details are set forth in order to provide a thorough understanding of one or more embodiments. It may be evident; however, that such embodiment(s) may be practiced without these specific details. Like numbers refer to like elements throughout.

Various embodiments or features will be presented in terms of systems that may include a number of devices, components, modules, and the like. It is to be understood and appreciated that the various systems may include additional devices, components, modules, etc. and/or may not include all of the devices, components, modules, etc. discussed in connection with the figures. A combination of these approaches may also be used.

Thus, methods and systems and the like are herein disclosed that provide for preparation of calibrant infusion fluid sources. In one embodiment, discussed in detail infra. a precise volume of glucose is injected into a saline-solution filled calibrant infusion fluid source proximate in time to conducting a calibration procedure. The glucose concentration in the calibrant infusion fluid source is subsequently calculated based on the measured weight of the saline-solution, as determined prior to glucose injection, and the volume of glucose injected. As exemplified herein, glucose is disclosed as calibrant (e.g., analyte of interest) for an intravenous blood glucose sensor system, however, essentially any analyte or combination of analytes of interest may be used as calibrant(s) in the infusion fluid source. Thus, hereinafter, the use of "glucose" as the calibrant is understood to be readily interchanged or combined with one or more other analytes of interest. This method provides a highly accurate and convenient manner for use in a hospital environment. In another embodiment, discussed in detail infra. a premixed calibrant infusion fluid source is provided that includes saline solution and a predetermined concentration of glucose. In such embodiments, shelf life problems related to water evaporation are mitigated by hermetically covering or otherwise hermetically containing the calibrant infusion fluid source up until the point of use. This procedure insures that the glucose concentration in the calibrant infusion fluid source is consistent with the concentration at the time of premix.

In one aspect of the present invention, the intravenous blood glucose (IVBG) sensor system illustrated in FIG. 1 is employed. System 100 of FIG. 1 includes a sensor assembly 102, for example, as described in U.S. patent application Ser. No. 11/691,432, filed Mar. 26, 2007, which is incorporated herein by reference, that is intravenously inserted to a patient 104. The sensor assembly 102 is connected to the patient via an intravenous (IV) port 106 and an infusion line 108, which is operably connected to a fluid controller (not shown) that is controlled by a control unit 110. Finally, the infusion line 108 continues upstream of the fluid controller to a calibrant infusion fluid source 112, such as a calibrant infusion fluid bag, which may be supported by member 114. The system may be attached to a support structure 116. In one embodiment, member 114 may serve as a scale (piezoelectric or spring) operable to weigh the bag and send the weight to the controller.

During calibration mode of system 100, control unit 110 controls and meters calibrant infusion fluid from the calibrant infusion fluid source 112, past sensor assembly 102, and into the patient 104. The sensor assemblies preferably include sensing electrodes constructed, for example, as described in United States Patent Publication No. 2007/0027384, which is incorporated herein by reference, and during calibration, the current generated by the respective electrodes of the sensor (e.g., a working electrode and a blank electrode) assembly is measured to provide calibration measurements for system 100.

During measurement mode of the system, blood is urged past the sensor, for example, by reversing the fluid controller. In one aspect, blood may be prevented from being withdrawn from the patient 104. In another aspect, blood from the patient may be drawn past sensor assembly 102 but preferably not past control unit 110. While blood is in contact with the sensor assembly the current generated by the respective electrodes is measured.

In one embodiment, substantially the same flow rates are used during calibration mode and during measurement mode. More particularly, the control system controls the infusion of the system such that the calibrant infusion fluid is urged past the sensor electrodes at a fixed flow rate during calibration, and the blood measurement is taken while the blood is drawn back from the patient at approximately the same flow rate. Other flow rates for the calibration and measurement modes may be used.

The calibrant infusion fluid may be repeatedly presented to the sensor, for example, in fixed or random time intervals, to provide calibrant-related signals suitable for calibrating the sensor. Any type of calibration protocol may be used to calibrate the sensor and may be based on one or more signals generated by any of the sensor electrodes upon exposure to the calibrant infusion fluid. The systems disclosed herein may be used in combination with any of the methods of preparing a calibrant infusion fluid source as disclosed and described herein.

Referring to FIG. 2, a flow diagram is presented of a method 200 for preparing a calibrant infusion fluid source, in accordance with embodiments of the present invention. At Event 210, a calibrant infusion fluid source that includes a saline solution is provided. In an alternate embodiment, the calibrant infusion fluid source additionally includes an anti-clotting agent, such as heparin or the like. In one specific embodiment, the calibrant infusion fluid source includes 1000 units of heparin in a 500 mL volume of 0.9 percent by weight sodium chloride (NaCl)

At Event 220, the weight of the content of the calibrant infusion fluid source is determined. According to one embodiment, the weight of the content is determined by weighing the calibrant infusion fluid source and subtracting the known weight of an empty calibrant infusion fluid source.

At Event 230, a predetermined volume of a predetermined glucose concentrate is added to the calibrant infusion fluid source. It should be noted that determination of the weight of the content of the calibrant infusion fluid source and addition of the glucose concentrate occurs proximate in time to a calibration or flush procedure to limit the effects of water vapor diffusion through the calibrant infusion fluid source, thereby insuring the accuracy of the resulting concentration of glucose in the calibrant infusion fluid source. According to one embodiment, the glucose concentrate is added to the calibrant infusion fluid source by injecting the predetermined volume of the predetermined glucose concentrate into the calibrant infusion fluid source using a syringe. In one specific embodiment, the syringe may include a volume-controlling mechanism, such as a dimpled "stop" or a tapered barrel or the like to accurately control the volume of glucose injected into the calibrant infusion fluid source. Testing has shown, as described below, that use of a syringe with a volume controlling mechanism, such as a dimpled "stop" results in greater consistency in the resultant calibrant infusion fluid source.

Additionally, according to specific embodiments, the syringe that is used for the injection may further be defined as a previously un-used syringe, i.e., a new syringe is used for each injection into a calibrant infusion fluid source. Also, according to other specific embodiments, the injection process is conducted as a single injection absent any additional syringe flushes into the calibrant infusion fluid source. Testing has shown, as described below, that use of a previously un-used syringe and conducting the injection absent any flush increases the consistency and accuracy of the injection process.

The amount of predetermined volume of glucose that is added to the calibrant infusion fluid source is proportional to the predetermined concentration of the glucose. Thus, if higher concentrate glucose is used, a smaller volume of glucose is added and if a lower concentrate glucose is used, a larger volume of glucose is added. According to certain embodiments of the invention, as described infra., adding/injecting lower concentration glucose in higher volume provides for greater overall reliability than adding/injecting higher concentration glucose in lower volume. In one specific embodiment of the invention, 5% (by weight) dextrose injections are used as the predetermined glucose concentrate, however, it should be noted that concentrations up to and exceeding 50% dextrose/glucose may also be used. In one embodiment, in which the calibrant infusion fluid sources contain 500 mL of saline and heparin solution, the 5% dextrose-injections are of 24 mL in volume.

At Event 240, the concentration of glucose in the calibrant infusion fluid source is determined based on the content weight of the calibrant infusion fluid source and the predetermined volume of glucose concentrate added/injected into the calibrant infusion fluid source. It is noted that the determination of the glucose concentration is a calculation based on the content weight of the calibrant infusion fluid source and the predetermined volume of glucose concentrate added/injected into the calibrant infusion fluid source as opposed to a measurement made by an analytical device, such as YSI 2300 Stat Plus, Gem Premier 3000 or the like. According to specific embodiments, once the concentration of the glucose in the calibrant infusion fluid source has been calculated, the calculated value is entered into or otherwise provided to analyte detection system, such as an intravenous blood glucose system for subsequent calibration purposes.

Referring to FIG. 3 a flow diagram is presented of an alternate method 300 for preparing a calibrant infusion fluid source in accordance with embodiments of the present invention. According to this alternate method, the calibrant infusion fluid source may be prepared well in advance of their use. In this regard, the calibrant infusion fluid source may be referred to as "pre-mixed" sources that do not require adding/injection glucose proximate in time to their use. At Event 310, a calibrant infusion fluid source is provided that includes a saline solution and a predetermined concentration of glucose. Additionally, the calibrant infusion fluid source may include an anti-clotting agent, such as heparin or the like to mitigate thrombus. Anti-clotting agents include any suitable anti-thrombotic agents such as, anti-platelet agents, thrombolytic agents, and non-heparin anticoagulants such as direct thrombin inhibitors and the like. In one specific embodiment, the calibrant infusion fluid source includes 1000 units of heparin in a 500 mL volume of 0.9 percent by weight sodium chloride (NaCl).

At Event 320, a hermetic containment is applied to the calibrant infusion fluid source. In one embodiment, applying the hermetic containment includes wrapping the calibrant infusion fluid source in a hermetic wrapping, such as a metalized plastic, a metalized foil or the like. In another embodiment, applying the hermetic containment includes placing the calibrant infusion fluid source in a metalized bag, which, according to certain embodiments, is heat-sealable. The purpose of the hermetic containment is to mitigate, lessen and/or eliminate water vapor diffusion from occurring through the calibrant infusion fluid source during the shelf life of the calibrant infusion fluid source. Over time, water will evaporate out of the calibrant infusion fluid source causing the concentration of the glucose in the calibrant infusion fluid source to fluctuate.

At Event 330, the hermetic containment is removed from the calibrant infusion fluid source proximate in time to using the calibrant infusion fluid source, i.e., conducting a calibration procedure or the like. As noted, use of the hermetic containment lessens or otherwise prohibits the occurrence of water vapor diffusion occurring to the shelf life of the pre-mixed calibrant infusion fluid sources. By lessening or otherwise prohibiting water vapor diffusion from occurring, the glucose concentration remains relatively consistent throughout the shelf life and, therefore, the need to calculate or otherwise measure the glucose concentration in the calibrant infusion fluid source prior to using the calibrant infusion fluid source is eliminated.

In combination with any of the above systems and methods, the calibrant infusion fluid source may be labeled with instructions for use (IFU). For example, the calibrant infusion fluid source may be labeled with IFU detailing the Events of FIG. 2. The instructions for use may be presented on the outside surface of the infusion fluid source and may be of any form, including for example, text, symbols, diagrams or combinations thereof.

Design of Experiments (1.-4.)

1. Altering the Concentration of the Glucose Injected in the Saline Solution-Filled Calibrant Infusion Fluid Source—YSI Measurements Experimentation was undertaken to evaluate differences exhibited by altering the concentration of glucose injected into the saline solution-filled calibrant infusion fluid sources, subsequently measuring the glucose concentration in the calibrant infusion fluid source using certifiable external equipment, such as for example, Yellow Springs Instrument 2300 STAT Plus™ Glucose & Lactate Analyzer (YSI) measurements and comparing the YSI measurements to calculated glucose concentrations. The rationale behind the experimentation is that a larger volume of a less concentrated glucose solution presents less opportunity for processing error than a smaller volume of a more concentrated solution.

Accordingly, this experiment utilized (1) a 50 percent glucose/50 percent water solution, specifically a 50 percent dextrose solution, referred to herein as D50W and (2) a 5.0 percent glucose/94.1 percent water/0.9 percent sodium chloride (NaCl), specifically a 5.0 percent dextrose solution, referred to herein as D5W.

Fifty (50) bags of heparin saline solution-filled calibrant infusion fluid sources were used in the experiment. Specifically, the calibrant infusion fluid sources contained Heparin Sodium 1000 Units in 0.9% by weight Sodium Chloride Injection (500 milliliter). Each calibrant infusion fluid source was weighed using a calibrated balance and the weight of the contents was determined and recorded.

After weighing the calibrant infusion fluid sources, a 3 milliliter (mL) syringe and a 16 gauge needle was used to inject 2.4 mL of 50 percent dextrose solution into calibrant infusion fluid sources designated as bags 1-25. Additionally, a 60 ml syringe and 16 gauge needle was used to inject 24 mL of 5 percent dextrose/0.9 percent NaCl solution into calibrant infusion fluid sources designated as bags 30-50. It should be noted that calibrant infusion fluid sources designated as bags 26-29 were not injected with either the 50% dextrose solution or the 5% dextrose solution.

The injection process proceeded pursuant to the following methodology. The syringe was flushed into and out of the calibrant infusion fluid source five times after the initial injection. After the initial injection and flushing process, the syringe was removed from the calibrant infusion fluid source and the calibrant infusion fluid source was shaken for a minimum of 20 seconds. After the shaking procedure, the needle was re-inserted into the calibrant infusion fluid source, flushed two more times and then removed from the calibrant infusion fluid source. The calibrant infusion fluid source was then shaken for an additional minimum of 10 seconds to insure thorough mixing of the solution. It should be noted that the same syringe and needle was used for each 50% dextrose injection (i.e., calibrant bags 1-25) and each 5% dextrose injection (i.e., calibrant bags 30-50). All residual solution remaining in the needle tip was expelled before drawing more dextrose for subsequent injections into another calibrant infusion fluid source.

After the injection process, triplicate 1.0 mL samples were drawn from each of the calibrant infusion fluid sources for the purpose of conducting YSI measurements glucose concentration measurements. For the purposes of this experimentation a YSI 2300 STAT Plus™ Glucose & Lactate Analyzer was implemented. For each 1.0 mL sample a fresh syringe was used. A single needle (different from the needle used for injection) was used for each of the 50% dextrose injected calibrant infusion fluid sources (i.e., calibrant bags 1-25) and another single needle (different from the needle used for injection) was used for each of the 5% dextrose injected calibrant infusion fluid sources (i.e., calibrant bags 30-50). All residual solution in the needle tip was expelled prior to conducting a sample draw.

FIG. 4 provides a plot of calibrant infusion fluid source weight in grams for each of the fifty (50) heparin saline solution-filled calibrant infusion fluid sources prior to injection of the glucose concentrate. As noted in FIG. 4, the mean weight of the heparin saline solution-filled calibrant infusion fluid source prior to injection of the glucose concentrate is 559.3 grams with a 0.31% standard deviation. Thus, the variability in the calibrant infusion fluid sources should be a negligible factor in the consistency of the injection process.

It is noted that the weight of each calibrant infusion fluid source's contents was calculated by subtracting 17 grams from the weight of each calibrant infusion fluid source, in order to compensate for the weight of the empty calibrant infusion fluid source. This adjusted weight is used to calculate subsequent glucose values.

FIG. 5 provides a plot of the triplicate glucose concentration measurements, i.e., YSI measurements; YSI1, YSI2, and YSI3, for heparin saline solution-filled calibrant infusion fluid sources filled with 50% dextrose, i.e., calibrant bags 1-25. The calculated glucose values were adjusted for the density of saline (1.00072 g/mL) and for the density of hydrous dextrose (hydrous dextrose Molecular Weight (MW)=0.9×dextrose MW). Thus, the calibrant infusion fluid source adjusted glucose concentration for 50% dextrose= (2.4×0.5×0.9)/(source contents weight×1.0072/1000)×100 milligrams per deciliter (mg/dL).

FIG. 6 provides a plot of the triplicate glucose concentration measurements, i.e., YSI measurements; YSI1, YSI2, and YSI3, for heparin saline solution-filled calibrant infusion fluid sources filled with 5% dextrose, i.e., calibrant bags 30-50. The calculated glucose values were adjusted for the density of saline (1.00072 g/mL) and for the density of hydrous dextrose (hydrous dextrose Molecular Weight (MW)=0.9×dextrose MW). Thus, the calibrant infusion fluid source adjusted glucose concentration for 5% dextrose=((24× 0.05×0.9)/(contents weight×1.0072/1000)×100 milligrams per deciliter (mg/dL).

The mean values, standard deviation values amongst triplicate samples and between calibrant infusion fluid sources and percent standard deviation values amongst triplicate samples and between calibrant infusion fluid sources for both the 50% dextrose solution and the 5% dextrose solution are reflected in Table 1.

TABLE 1

| | YSI Measured Glucose Concentration | | | | |
|---|---|---|---|---|---|
| | Mean | Among Triplicates | | Between Bags | |
| | (mg/dL) | Std Dev (mg/dL) | % Std Dev | Std Dev (mg/dL) | % Std Dev |
| D50W | 207.9 | 1.06 | 0.52% | 10.02 | 4.82% |
| D5W | 189.2 | 1.49 | 0.66% | 1.55 | 0.82% |

Thus, as shown by the results in FIG. 5, FIG. 6 and Table 1, when either 50% dextrose or 5% dextrose was injected into the heparin saline solution-filled calibrant infusion fluid sources, the glucose concentration measurements are very consistent within each triplicate sample set, as indicated by the associated mean percent standard deviation of 0.52% for 50% dextrose measurements and 0.66% for 5% dextrose measurements. This indicates good overall consistency of the solution in both the 50% dextrose-injected heparin saline solution-filled calibrant infusion fluid sources and the 5% dextrose-injected heparin saline solution-filled calibrant infusion fluid sources. However, between source to source, the mean percent standard deviation for 50% dextrose prepared sources is quantifiably greater than that of the 5% dextrose prepared sources. For the 50% dextrose-injected heparin saline solution-filled calibrant infusion fluid sources, the percent standard deviation for the YSI measured glucose concentration among all sources is 4.82%. In contrast, for the 5% dextrose-injected heparin saline solution-filled calibrant infusion fluid sources, the percent standard deviation for the YSI measured glucose concentration among all sources is 0.82%. This shows that the process of calibrant infusion fluid source preparation is more consistent at the lower dextrose concentration, i.e., 5% dextrose than at the higher dextrose concentration, i.e., 50%.

The actual collected data for 50% dextrose-injected heparin saline solution-filled calibrant infusion fluid sources, i.e., calibrant bags 1-25, is reflected in the table of FIG. 8 and the actual collected data for 5% dextrose-injected heparin saline solution-filled calibrant infusion fluid sources, i.e., calibrant bags 30-50 is reflected in the table of FIG. 9. The actual collected data includes, the weight of the calibrant infusion fluid source prior to injection, the adjusted weight of the calibrant infusion fluid source's contents, triplicate sample glucose concentration measurements (YSI1, YSI2 and YSI3), the mean of the triplicate sample measurements, the standard deviation of the triplicate sample measurements, the percent standard deviation of the triplicate sample measurements, source adjusted glucose concentration, the standard deviation of the source adjusted glucose concentration, the percent standard deviation of the source adjusted glucose concentration.

FIG. 7 provides a plot of the percentage delta between the mean YSI value and the source adjusted calculated glucose value of all forty-five (45) dextrose injected heparin saline solution-filled calibrant infusion fluid sources. As depicted in FIG. 7, the YSI measurements for 50% dextrose-injected heparin saline solutions tend to read higher than corresponding calculated glucose concentrations. Conversely, the YSI measurements for 5% dextrose-injected saline solutions read lower than corresponding calculated glucose concentrations. Additionally, there is more variability observed between the measurement of calibrant infusion fluid sources injected with 50% dextrose than those injected with 5% dextrose.

The mean percentage delta between the mean YSI value and the calculated glucose value, and the highest and lowest percentage delta between the mean YSI value and the calculated glucose value for the 50% dextrose injected heparin saline solution-filled calibrant infusion fluid sources and the 5% dextrose heparin saline solution-filled calibrant infusion fluid sources are reflected in Table 2.

TABLE 2

| | Mean % Δ, Δ/(200 mg/dL) | Highest % Δ | Lowest % Δ |
|---|---|---|---|
| D50W | 5.03% | 17.07% | −3.92% |
| D5W | −4.24% | −3.22% | −5.39% |

As shown in Table 2, YSI measurements drawn from the 50% dextrose heparin saline solution-filled calibrant infusion fluid sources range from about 4% lower up to about 17% higher than the calculated glucose value. In contrast, YSI measurements drawn from the 5% heparin saline solution-filed calibrant infusion fluid sources range from about 3% to about 5% lower than the calculated glucose value. It should be noted that since the targeted glucose concentration equals 200 mg/dL, the actual percent range is from about 1.6% to about 2.7%.

Thus, based on the described experimentation the following conclusions can be drawn. (1) The variability in the content weights prior to glucose injection is not an aspect of concern for the consistency of the dextrose injection process because, as shown in FIG. 4, the content weights are consistent. (2) The consistency of the triplicate sample readings for each glucose injected heparin saline solution-filled calibrant infusion fluid source demonstrates that the YSI measurement can provide reproducible results. (3) 50% dextrose-injected heparin saline solution-filled calibrant infusion fluid sources may not be as reproducible as 5% dextrose-injected heparin saline solution-filled calibrant infusion fluid sources, based on the percent difference between YSI readings and calculated glucose values being significantly larger for 50% dextrose-injected sources than for 5% dextrose-injected sources. (4) A larger volume of a less concentrated dextrose solution appears to provide a more reliable system for heparin saline solution calibrant infusion fluid source preparation.

2. Altering the Concentration of the Glucose Injected in the Saline Solution-Filled Calibrant Infusion Fluid Source—GEM Premier 3000 Measurements Experimentation was undertaken to evaluate differences exhibited by altering the concentration of glucose injected into the saline solution-filled calibrant infusion fluid sources, subsequently measuring the glucose concentration in the calibrant infusion fluid source using GEM measurements and comparing the GEM measurements to calculated glucose concentrations. Similar to the experimentation undertaken using YSI measurements, the rationale behind this experimentation is that a larger volume of a less concentrated glucose solution presents less opportunity for processing error than a smaller volume of a more concentrated solution.

Accordingly, this experiment utilized (1) a 50 percent glucose/50 percent water solution, specifically a 50 percent dextrose solution, referred to herein as D50W and (2) a 5.0 percent glucose/94.1 percent water/0.9 percent sodium chloride (NaCl), specifically a 5.0 percent dextrose solution, referred to herein as D5W.

Fifty (50) bags of heparin saline solution-filled calibrant infusion fluid sources were used in the experiment. Specifically, the calibrant infusion fluid sources contained Heparin Sodium 1000 Units in 0.9% by weight Sodium Chloride Injection (500 milliliter). Each calibrant infusion fluid source was weighed using a calibrated balance and the weight of the contents was determined and recorded. It should be noted that the same identical heparin saline-solution-filled calibrant infusion fluid sources used in the YSI measurement experiment were used for GEM measurements. For the purpose of assuring a realistic comparison between the YSI measurements and the GEM measurements, the GEM measurements were made immediately after the triplicate YSI measurements were completed for each source.

After weighing the calibrant infusion fluid sources, a 3 milliliter (mL) syringe and a 16 gauge needle was used to inject 2.4 mL of 50 percent dextrose solution into calibrant infusion fluid sources designated as bags 1-25. Additionally, a 60 ml syringe and 16 gauge needle was used to inject 24 mL of 5 percent dextrose/0.9 percent NaCl solution into calibrant infusion fluid sources designated as bags 30-50. It should be noted that calibrant infusion fluid sources designated as bags 26-29 were not injected with either the 50% dextrose solution or the 5% dextrose solution.

The injection process proceeded pursuant to the following methodology. The syringe was flushed into and out of the calibrant infusion fluid source five times after the initial injection. After the initial injection and flushing process, the syringe was removed from the calibrant infusion fluid source and the calibrant infusion fluid source was shaken for a minimum of 20 seconds. After the shaking procedure, the needle was re-inserted into the calibrant infusion fluid source, flushed two more times and then removed from the calibrant infusion fluid source. The calibrant infusion fluid source was then shaken for an additional minimum of 10 seconds to insure thorough mixing of the solution. It should be noted that the same syringe and needle was used for each 50% dextrose injection (i.e., calibrant bags 1-25) and each 5% dextrose injection (i.e., calibrant bags 30-50). All residual solution remaining in the needle tip was expelled before drawing more dextrose for subsequent injections into another calibrant infusion fluid source.

After the injection process, triplicate 1.0 mL samples were drawn from each of the sources for the purpose of conducting GEM glucose concentration measurements. For the purposes of this experimentation a GEM premier 3000 analyzer was implemented. For each 1.0 mL sample a fresh syringe was used. A single needle (different from the needle used for injection) was used for each of the 50% dextrose injected bags (i.e., calibrant bags 1-25) and another single needle (different from the needle used for injection) was used for each of the 5% dextrose injected bags (i.e., calibrant bags 30-50). All residual solution in the needle tip was expelled prior to conducting a sample draw.

FIG. 10 provides a plot of calibrant infusion fluid source weight in grams for each of the fifty (50) heparin saline solution-filled calibrant infusion fluid sources prior to injection of the glucose concentrate. As noted in FIG. 10, the mean weight of the heparin saline solution-filled calibrant infusion fluid sources prior to injection of the glucose concentrate is 559.3 grams with a 0.31% standard deviation. Thus, the variability in the calibrant infusion fluid sources should be a negligible factor in the consistency of the injection process.

It is noted that the weight of each source's contents was calculated by subtracting 17 grams from the weight of each source, in order to compensate for the weight of the empty calibrant infusion fluid source bag. The adjusted weight (i.e., the weight of the source's contents) is subsequently used to calculate all glucose values.

FIG. 11 provides a plot of the triplicate glucose concentration measurements, i.e., GEM measurements; GEM1, GEM2, and GEM3, for heparin saline solution-filled calibrant infusion fluid sources filled with 50% dextrose, i.e., calibrant bags 1-25. The calculated glucose values were adjusted for the density of saline (1.00072 g/mL) and for the density of hydrous dextrose (hydrous dextrose Molecular Weight (MW)=0.9×dextrose MW). Thus, the source adjusted glucose concentration for 50% dextrose=(2.4×0.5×0.9)/(source contents weight×1.0072/1000)×100 milligrams per deciliter (mg/dL). For the heparin saline solution-filled sources injected with 50% dextrose, the GEM reads higher than the targeted 200 mg/dL.

FIG. 12 provides a plot of the triplicate glucose concentration measurements, i.e., GEM measurements; GEM1, GEM2, and GEM3, for heparin saline solution-filled calibrant infusion fluid sources filled with 5% dextrose, i.e., calibrant bags 30-50. The calculated glucose values were adjusted for the density of saline (1.00072 g/mL) and for the density of hydrous dextrose (hydrous dextrose Molecular Weight (MW)=0.9×dextrose MW). Thus, the source adjusted glucose concentration for 5% dextrose ((24×0.056×0.9/ (source contents weight×1.0072/1000)×100 milligrams per deciliter (mg/dL). For the heparin saline solution-filled sources injected with 5% dextrose, the GEM reads higher than the targeted 200 mg/dL.

The mean values, standard deviation values amongst triplicate samples and between calibrant infusion fluid sources and percent standard deviation values amongst triplicate samples and between calibrant infusion fluid sources for both the 50% dextrose solution and the 5% dextrose solution are reflected in Table 3.

TABLE 3

| | Gem Premier 3000 | | | | |
|---|---|---|---|---|---|
| | Mean | Between Triplicates | | Between Bags | |
| | (mg/dL) | Std Dev (mg/dL) | Std Dev (%) | Std Dev (mg/dL) | Std Dev (%) |
| D50W | 220.5 | 0.9 | 0.41% | 9.20 | 4.17% |
| D5W | 191.6 | 1.1 | 0.57% | 2.82 | 1.47% |

Thus, as shown by the results in FIG. 11, FIG. 12 and Table 3, when either 50% dextrose or 5% dextrose was injected into the heparin saline solution-filled calibrant infusion fluid sources, the glucose concentration measurements are very consistent within each triplicate sample set, as indicated by the associated mean percent standard deviation of 0.41% for 50% dextrose measurements and 0.57% for 5% dextrose measurements. This indicates good overall consistency of the solution in both the 50% dextrose-injected heparin saline solution-filled calibrant infusion fluid sources and the 5% dextrose-injected heparin saline solution-filled calibrant infusion fluid sources. However, between source to source, the mean percent standard deviation for 50% dextrose prepared calibrant infusion fluid sources is quantifiably greater than that of the 5% dextrose prepared sources. For the 50% dextrose-injected heparin saline solution-filled calibrant infusion fluid sources, the percent standard deviation for the GEM measured glucose concentration among all sources is 4.17%. In contrast, for the 5% dextrose-injected heparin saline solution-filled calibrant infusion fluid sources, the percent standard deviation for the GEM measured glucose concentration among all sources is 1.47%. This shows that the process of source preparation is more consistent at the lower dextrose concentration, i.e., 5% dextrose than at the higher dextrose concentration, i.e., 50%.

The actual collected data for 50% dextrose-injected heparin saline solution-filled calibrant infusion fluid sources, i.e., calibrant sources 1-25, is reflected in the table of FIG. 14 and the actual collected data for 5% dextrose-injected heparin saline solution-filled calibrant infusion fluid sources, i.e., calibrant sources 30-50 is reflected in the table of FIG. 15. The actual collected data includes, the weight of the source prior to injection, the adjusted weight of the source's contents, triplicate sample glucose concentration measurements (GEM1, GEM2 and GEM3), the mean of the triplicate sample measurements, the standard deviation of the triplicate sample measurements, the percent standard deviation of the triplicate sample measurements, source adjusted glucose concentration, the standard deviation of the source adjusted glucose concentration, the percent standard deviation of the source adjusted glucose concentration.

FIG. 13 provides a plot of the percentage delta between the mean GEM value and the calibrant infusion fluid source adjusted calculated glucose value of all forty-five (45) dextrose injected heparin saline solution-filled calibrant infusion fluid sources. As depicted in FIG. 13, there is more variability observed between the measurement of sources injected with 50% dextrose than those injected with 5% dextrose.

The mean percentage delta between the mean GEM value and the calculated glucose value, and the highest and lowest percentage delta between the mean GEM value and the calculated glucose value for the 50% dextrose injected heparin saline solution-filled calibrant infusion fluid sources and the 5% dextrose heparin saline solution-filled calibrant infusion fluid sources are reflected in Table 4.

TABLE 4

| | Mean % Δ, Δ/(200 mg/dL) | % Max Δ | % Min Δ |
|---|---|---|---|
| D50W | 11.32% | 23.90% | 6.25% |
| D5W | −3.02% | 0.47% | −5.39% |

As shown in Table 4, GEM measurements drawn from the 50% dextrose heparin saline solution-filled calibrant infusion fluid sources range from about 6% up to about 24% higher than the calculated glucose value. In contrast, YSI measurements drawn from the 5% heparin saline solution-filled calibrant infusion fluid sources range from about 5% lower to about 0.5% higher than the calculated glucose value.

A comparison of the percentage delta values between the mean GEM and YSI values to the source adjusted calculated glucose values of dextrose injected heparin saline solution-filled sources is presented in Table 5.

TABLE 5

| | GEM Premier 3000 Data | | | | YSI 2300 Stat Plus Data | | | |
|---|---|---|---|---|---|---|---|---|
| | Mean %Δ, Δ/(200 mg/dL) | Highest %Δ | Lowest %Δ | Range (Highest %Δ − Lowest %Δ) | Mean %Δ, Δ/(200 mg/dL) | Highest %Δ | Lowest %Δ | Range (Highest %Δ − Lowest %Δ) |
| D50W | 11.32% | 23.90% | 6.25% | 17.65% | 5.03% | 17.07% | −3.92% | 20.98% |
| D5W | −3.02% | 0.47% | −5.39% | 5.86% | −4.24% | −3.22% | −5.39% | 2.17% |

As shown in Table 5, both the mean percentage delta GEM readings and the mean percentage delta YSI readings for the 50% injected heparin saline solution-filled calibrant infusion fluid sources read on average higher than the calculated glucose values. In contrast, for the 5% dextrose-injected heparin saline solution-filled calibrant infusion fluid sources, both the YSI readings and the GEM readings are on average lower than the calculated glucose values. The mean percentage delta for the 50% dextrose-injected heparin saline solution-filled calibrant infusion fluid sources on the GEM is notably higher than on the YSI. The mean percentage deltas for the 5% dextrose-injected heparin saline solution-filled calibrant infusion fluid sources are comparable for both YSI and GEM.

For the 50% dextrose-injected saline solution-filled calibrant infusion fluid sources, the range between the highest and lowest percentage delta for the GEM and YSI are 17.65% and 20.98%, respectively. For the 5% dextrose-injected heparin saline solution-filled calibrant infusion fluid sources, the range between the highest and the lowest percentage delta for the GEM and YSI are 5.86% and 2.17%, respectively. The consistency of the low percentage delta for the 5% dextrose-injected heparin saline solution-filled calibrant infusion fluid sources on both YSI and GEM instrumentation indicates that the process of injection using the lower dextrose concentration yields more reliability than using the higher dextrose concentration Thus, based on the described experimentation the following conclusions can be drawn. (1) The consistency of the triplicate sample readings for each glucose injected heparin saline solution-filled calibrant infusion fluid source demonstrates that the GEM measurement can provide reproducible results. (2) 50% dextrose-injected heparin saline solution-filled calibrant infusion fluid sources may not be as reproducible as 5% dextrose-injected heparin saline solution-filled calibrant infusion fluid sources, based on the percent difference between GEM readings and calculated glucose values being significantly larger for 50% dextrose-injects sources than for 5% dextrose-injected sources. (3) A larger volume of a less concentrated dextrose solution as opposed to a smaller volume of a higher concentrated dextrose solution appears to provide a more reliable system for heparin saline solution calibrant infusion fluid source preparation.

3. Dimpled Versus Non-Dimpled Syringes

Experimentation was undertaken to evaluate the affects of using dimpled and non-dimpled syringes for injecting glucose into heparin saline solution-filled calibrant infusion fluid sources. By implementing the use of dimpled syringes, the variability of the dextrose volume injected into each heparin saline solution-filled calibrant infusion fluid source may be lowered because the dimpled syringe is designed to hold and inject a specified volume due to its dimpled "stop", which limits how far the syringe plunger can be pulled back during the draw process.

Forty (40) bags of heparin saline solution-filled calibrant infusion fluid sources were used in the experiment. Specifically, the calibrant infusion fluid sources contained Heparin Sodium 1000 Units in 0.9% by weight Sodium Chloride Injection (500 milliliter). Each calibrant infusion fluid source was weighed using a calibrated balance and the weight of the contents was determined and recorded.

After weighing the calibrant infusion fluid sources, a 3 milliliter (mL) syringe dimpled at 1.5 mL and a 16 gauge needle were used to inject 1.5 mL of 50 percent dextrose solution into calibrant infusion fluid sources designated as bags 1-20. Additionally, a 3 mL non-dimpled syringe and 16 gauge needle were used to inject 1.5 mL of 50 percent dextrose solution into calibrant infusion fluid sources designated as bags 21-40.

The injection process proceeded pursuant to, the following methodology. The syringe was injected and removed from each the calibrant infusion fluid source. After the injection, the calibrant infusion fluid source was shaken for a minimum of 20 seconds. No flush was performed after the injection. The same needle and a new dimpled syringe were used for each dimpled syringe dextrose injection. The same needle and a new non-dimpled syringe were used for each of the non-dimpled syringe dextrose injections. All residual solution in the needle tip was expelled before drawing more dextrose for subsequent injections into another calibrant infusion fluid source. Each syringe was labeled with a source identifier and saved for subsequent weight/volume testing.

After the injection process, triplicate 1.0 mL samples were drawn from each of the sources for the purpose of conducting YSI glucose concentration measurements. For each 1.0 mL sample a fresh syringe was used. A single needle (different from the needle used for injection) was used for all of the drawn samples. All residual solution in the needle tip was expelled prior to conducting a sample draw.

FIG. 16 provides a plot of source weight in grams for each of the forty (40) heparin saline solution-filled calibrant infusion fluid sources prior to injection of the glucose concentrate. As noted in FIG. 16, the mean weight of the heparin saline solution-filled calibrant infusion fluid sources prior to injection of the glucose concentrate is 558.7 grams with a 0.33% standard deviation. The variability of the weights of the heparin saline solution-filled sources is relatively low. The source weights range from a low of 555 grams to a high of 564 grams. Thus, the variability in the sources should be a negligible factor in the consistency of the dextrose injection process.

It is noted that the weight of each source's contents was calculated by subtracting 17 grams from the weight of each source, in order to compensate for the weight of the empty calibrant infusion fluid source. The adjusted weight (i.e., the weight of the source's contents) is subsequently used to calculate all glucose values. Additionally, the calculated glucose values are adjusted for the density of saline (1.00072 g/mL) and for the hydrous dextrose (hydrous dextrose Molecular Weight (MW)=0.9×dextrose MW). Thus, the source adjusted glucose concentration for 50% dextrose=((1.5×0.5×0.9/(adjusted source weight×1.0072/1000)×100 milligrams per deciliter (mg/dL).

FIG. 17 provides a plot of the triplicate glucose concentration measurements, i.e., YSI measurements; YSI1, YSI2, and YSI3, for heparin saline solution-filled calibrant infusion fluid sources filled with 50% dextrose and injected using dimpled syringes, i.e., calibrant bags 1-20. FIG. 18 provides a plot of the triplicate glucose concentration measurements, i.e., YSI measurements; YSI1, YSI2, and YSI3, for heparin saline solution-filled calibrant infusion fluid sources filled with 50% dextrose and injected using non-dimpled syringes, i.e., calibrant bags 21-40. When either dimpled or non-dimpled syringes were used to inject the 50% dextrose-injection into the heparin saline solution-filled calibrant infusion fluid sources, the YSI readings within each triplicate set are relatively consistent. This testing further supports the conclusion that YSI can provide reproducible measurements.

The mean values, standard deviation values amongst triplicate samples and between sources and percent standard deviation values amongst triplicate samples and between sources for both the dimpled syringe injections and the non-dimpled syringe injections are reflected in Table 6.

TABLE 6

| | YSI Measured Glucose Concentration | | | | |
|---|---|---|---|---|---|
| | | Among Triplicates | | Between Bags | |
| Syringe Type | Mean (mg/dL) | Std Dev (mg/dL) | % Std Dev | Std Dev (mg/dL) | % Std Dev |
| Dimpled | 116.6 | 0.71 | 0.61% | 1.60 | 1.4% |
| Non-Dimpled | 124.6 | 0.96 | 0.77% | 2.45 | 2.0% |

Thus, as shown by the results in Table 6, the mean YSI measurement of the heparin saline solution-filled calibrant infusion fluid sources injected with 50% dextrose using a dimpled syringe and a non-dimpled syringe is 116.6 mg/dL and 124.6 mg/dL, respectively. The corresponding percent standard deviation among triplicate sets is 0.61% and 0.77% for the dimpled and non-dimpled injection measurements, respectively. The standard deviations between sources for the dimpled and non-dimpled syringe injections are also comparable.

The actual collected data for dimpled syringe-injected heparin saline solution-filled calibrant infusion fluid sources, i.e., calibrant bags 1-20, is reflected in the table of FIG. 20 and the actual collected data for non-dimpled-injected heparin saline solution-filled calibrant infusion fluid sources, i.e., calibrant bags 21-40 is reflected in the table of FIG. 21. The actual collected data includes, the weight of the source prior to injection, the adjusted weight of the source's contents, the source adjusted calculated glucose concentration, triplicate sample YSI measurements (Sample 1, Sample 2 and Sample 3), the mean of the triplicate sample measurements, the standard deviation of the triplicate sample measurements, the percent standard deviation of the triplicate sample measurements, mean YSI adjusted source glucose concentration delta, percentage delta and estimated percentage delta.

FIG. 19 provides a plot of the percentage delta between the mean YSI value and the source adjusted calculated glucose value for heparin saline solution-filled calibrant infusion fluid sources injected with 50% dextrose using dimpled (bags 1-20) and non-dimpled syringes (bags 21-40). As depicted in FIG. 19, the YSI measurements for heparin saline solution-filled calibrant infusion fluid sources injected with 50% dextrose using dimpled syringes tend to read lower than corresponding calculated glucose concentrations. The YSI measurements for heparin saline solution-filled calibrant infusion fluid sources injected with 50% dextrose using non-dimpled syringes on average read within 5% of the corresponding calculated glucose concentrations.

Table 7 provides a comparison between the percentage delta values between YSI and source adjusted calculated glucose for dimpled versus non-dimpled and the previously discussed experimentation of 50% dextrose-injection versus 5% dextrose-injection (i.e., Altering the Concentration of the Glucose Injected in the Saline Solution-Filled Calibrant Infusion Fluid Source—YSI Measurements).

TABLE 7

| Date of Experiment | Target Glucose | Syringe Type | New/Used Syringe | Flush/No Flush | Dextrose | Mean % Δ | Highest %Δ | Lowest %Δ | % Range |
|---|---|---|---|---|---|---|---|---|---|
| Jan. 29, 2009 | 125 mg/L | Dimpled | New | No flush | D50W | −5.6% | −2.1% | −7.3% | 5.2% |
| Jan. 30, 2009 | 125 mg/L | Non-Dimpled | New | No flush | D50W | 0.6% | 5.2% | −3.2% | 8.4% |
| Jan. 19, 2009 | 200 mg/dL | Non-Dimpled | Used | Flush | D50W | 5.03% | 17.07% | −3.92% | 21.0% |
| Jan. 20, 2009 | 200 mg/dL | Non-Dimpled | Used | Flush | D5W | −4.24% | −3.22% | −5.39% | 2.2% |

As illustrated by the data in Table 7, when the same non-dimpled syringe was used for the injection of 50% dextrose into heparin saline solution-filled calibrant infusion fluid sources and a syringe flush was performed, the range between the highest and lowest percentage delta was 21.0%. However, when a new, non-dimpled syringe was used for each injection of 50% dextrose and no flush performed, as in the case of the currently discussed experiment, the range between the highest and lowest percentage delta is 8.4% with a mean percentage delta of 0.6%. Therefore, a conclusion may be made that using a new syringe and omitting the flush for each injection increases the consistency and accuracy of the injection process.

Within the 50% dextrose injections as presented in Table 7, the lowest percent range of 5.2% occurred when a new, dimpled syringe was used for each injection and no flush was performed. Therefore, a conclusion may be made that using dimpled syringes provides more consistency in the resultant glucose source concentration.

Additionally, Table 7 compares the percentage delta and percent ranges from the two experiments using dimpled versus non-dimpled syringes and 50% dextrose-injections versus 5% dextrose-injections. Due to volume capacity of the dimpled syringes, this experiment had a target glucose value of 125 mg/dL, which is significantly lower than the target glucose value of 200 mg/dL from the previously discussed experiment. As shown in Table 8, in order to better compare the data, the percentage delta and percent range of the dimpled versus non-dimpled syringe experiment was recalculated to reflect a target of 200 mg/dL glucose.

TABLE 8

| | | Estimated % Delta for Target 200 mg/dL | | | | | Data from Jan. 19, 2009-Jan. 20, 2009 Study | | | | |
|---|---|---|---|---|---|---|---|---|---|---|---|
| Dextrose | Syringe Type | Mean %Δ | Highest %Δ | Lowest %Δ | % Range | Dextrose | Syringe Type | Mean %Δ | Highest %Δ | Lowest %Δ | % Range |
| D50W | Dimpled | −3.51% | −1.32% | −4.54% | 3.22% | D50W | Non-Dimpled | 5.03% | 17.07% | −3.92% | 21.0% |
| D50W | Non-Dimpled | 0.67% | 3.28% | −1.99% | 5.27% | D5W | Non-Dimpled | −4.24% | −3.22% | −5.39% | 2.2% |

As reflected in Table 8, an estimated percentage delta is projected for the dimpled and non-dimpled syringes when targeting for a 200 mg/dL glucose concentration. When the percent range of the dimpled syringe injection is thus adjusted, it becomes comparable to the percent range of the favorable 5% dextrose-injection. Additionally, the mean percentage delta of the dimpled syringe injection (−3.51%) becomes more comparable to that of the 5% dextrose-injection (−4.24%). Also, as depicted in Table 8, using a new syringe and not performing a flush reduces the mean percentage delta from 5.03% to an estimated 0.37%. These data indicate that the dimpled syringe provides the most consistent results while the method of implementing a new syringe and no flush following the injection provides the most accurate volume capacity of 1.5 mL per injection and omitting the subsequent flush may present accurate and precise results.

collected data includes triplicate DI water sample weights, mean weight, standard deviation, percent deviation, delta mean and percentage delta.

FIGS. 24 and 25 depict plots of the triplicate weights of 1.5 mL DI water samples dispensed from dimpled and non-dimpled syringes, respectively. As depicted, the weight measurements of the DI water dispensed from each syringe are consistent within each triplicate set. However, the weights of the DI water dispensed from the dimpled syringes tend to weigh less than the indicated 1.5 mL (based on the density of water being 1.0 g/mL and, therefore, 1.5 mL of water equals 1.5 g of water).

Referring to Table 9, shown is a comparison of the weights of 1.5 mL DI water dispensed from the dimpled and non-dimpled syringes.

TABLE 9

| | Weights of 1.5 mL DI Water Dispensed From Dimpled and Non-Dimpled Syringes | | | | | | | | |
|---|---|---|---|---|---|---|---|---|---|
| | | Among Triplicates | | | Between Syringes | | % Delta | | |
| Syringe Type | Mean (g) | Std Dev (g) | % Std Dev | Std Dev (g) | % Std Dev | Mean %Δ, Δ/1.5 g) | Highest %Δ | Lowest %Δ | % Range |
| Dimpled | 1.4735 | 0.0045 | 0.31% | 0.0107 | 0.72% | −1.77% | −0.62% | −3.12% | −2.49% |
| Non-Dimpled | 1.4971 | 0.0058 | 0.39% | 0.0101 | 0.68% | −0.19% | 0.68% | −2.39% | −3.08% |

Therefore, based on the described experimentation the following conclusions can be drawn. (1) Using a new syringe for each injection and not performing a flush after each injection greatly reduces the delta between the YSI measurements and the calculated glucose value. (2) The use of dimpled syringes provides more consistent results than the use of non-dimpled syringes.

4. Volume Analysis and Plunger Material Evaluation of Dimpled Syringes

Experimentation was undertaken to evaluate the variability of volume dispensed from dimpled and non-dimpled syringes. Previous experimentation had shown that a lower mean YSI measured glucose concentration resulted for dimpled syringe-injected heparin saline solution-filled calibrant infusion fluid sources. These results formed a hypothesis that the dimpled syringes may contain a consistently lower volume than the indicated 1.5 mL.

Experimentation was conducted on the forty (40) dimpled and non-dimpled syringes used in the previous experiment (Dimpled versus Non-Dimpled Syringes). A single 16 gauge needle was used for the draws and dispenses. The needle and each syringe were used to draw 1.5 mL from a beaker containing room temperature distilled (DI) water. After the draw, the DI water from the syringe was dispensed and weighed. Each syringe was subjected to the draw and weigh procedure in triplicate. Collected data for the dimpled and non-dimpled syringes is depicted in FIGS. 22 and 23, respectively. The The mean weight of the volume of water dispensed from the dimpled syringes and non-dimpled syringes are 1.4735 and 1.4971 grams, respectively. The corresponding percent standard deviation between syringes is 0.72% and 0.68% for the dimpled and non-dimples syringes, respectively. Additionally, it is noted that the mean percentage delta of the weights of the DI water dispensed form the dimpled syringes is −1.77% with a range of −2.49%. In comparison, the DI water weights dispensed from the non-dimpled syringes have a mean percentage delta of −0.019% and a range of −3.08%. Thus, the dimpled syringes consistently provide a volume less than indicated 1.5 mL.

FIG. 26 depicts a plot of the percentage delta between the mean weights of water dispensed from the dimpled and non-dimpled syringes and the indicated 1.5 mL target volume. As shown in FIG. 26, the percentage delta of the mean weights of 1.5 mL DI water dispensed from the dimpled syringes often reads lower than 0%. In contrast, the percentage delta of the mean weights of the 1.5 mL water dispensed from the non-dimpled syringes is significantly closer to 0%.

Table 10 presents a comparison of statistics between all dimpled syringes, all non-dimpled syringes and non-dimpled syringes with the exception of syringe No. 37. As shown in Table 10, while the triplicate weights of the measured water dispensed from syringe No. 37 are consistent; the percentage delta is much lower than the percentage delta of the DI water weights dispensed from all other non-dimpled syringes. This suggests that syringe No. 37 is an outlier in its ability to dispense 1.5 mL as indicated.

TABLE 10

|  | Mean (mL) | Std Dev (mL) | % Std Dev | Mean % Δ | % Range |
|---|---|---|---|---|---|
| Dimpled (All) | 1.4735 | 0.0107 | 0.72% | −1.77% | 2.49% |
| Non-Dimpled (All) | 1.4971 | 0.0101 | 0.68% | −0.19% | 3.08% |
| Non-Dimpled (#37 Omitted) | 1.4989 | 0.0064 | 0.43% | −0.07% | 1.40% |

As shown in Table 10, when the weights of the DI water dispensed from the No. 37 non-dimpled syringe are excluded from the data set, the mean volume increases from 1.4971 mL to 1.4989 mL. The percentage delta decreases accordingly from −0.19% to −0.07%, which is significantly lower than the delta of the weights of the DI water dispensed from the dimpled syringes. Additionally, with data attained from syringe No. 37 omitted, the percent range of the highest and lowest percentage delta values for the non-dimpled syringes also decreases from 3.08% to 1.40%. This finding suggests that the non-dimpled syringes can provide accurate and precise injections into the heparin saline calibrant sources. Considering the data set for both the volume dispensed from the dimpled and non-dimpled syringes, the percentage delta remains within about 3% of 1.5 mL, which is viewed as sufficient accuracy for 50% dextrose volume dispense.

Table 11 provides a comparison of YSI measured glucose concentration of the syringes and the syringes volume weights.

TABLE 11

| | YSI Measured Glucose Reported on Feb. 04, 2009 | | | Syringe Volume | | |
|---|---|---|---|---|---|---|
| Syringe Type | Mean YSI (mg/dL) | Mean %Δ | % Difference (Mean YSI Dimpled − Mean YSI Non-Dimpled)/Mean YSI | Mean Volume (mL) | Mean % Δ | % Difference (Mean Volume Dimpled − Mean Volume Non-Dimpled)/Mean Volume |
| Dimpled | 116.6 | −5.60% | 6.86% | 1.4735 | −1.77% | 1.60% |
| Non-Dimpled | 124.6 | −0.60% | 6.42% | 1.4971 | −0.19% | 1.58% |

As shown in Table 11, the mean percentage delta of the measured YSI glucose for the dimpled and non-dimpled syringes is −5.6% and 0.6%, respectively. The mean percentage delta of the syringe volume dispensed by the dimpled and non-dimpled syringes is −1.77% and −0.19%, respectively. This comparison of the percentage delta values illustrates that the volume dispensed from each syringe does not account for the difference in the YSI measured glucose concentration between sources prepared with dimpled and non-dimpled syringes. The percent difference between the mean YSI values and the mean volumes for the dimpled and non-dimpled syringes are not comparable, therefore, the dispensed dimpled syringe volume is not a direct cause of the lower glucose concentration value measured in the sources prepared with dimpled syringes.

Therefore, based on the described experimentation the following conclusions can be drawn. (1) The dimpled syringes deliver a volume less than an indicated 1.5 mL. In contrast, the non-dimpled syringe consistently dispenses a volume relatively proximate to 1.5 mL. However, the accuracy of the volume dispensed from the dimpled syringes is viewed as adequate for the intended application. (2) The lower glucose concentration of the heparin saline solution-filled calibrant infusion fluid sources injected with 50% dextrose using dimpled syringes is not a result of the lower syringe volume measured because the delta values of the mean YSI measured values and the percentage delta of the mean volumes dispensed by the dimpled syringes are not comparable.

Thus, present embodiments provide for methods and systems for preparation of calibrant infusion fluid sources. In one embodiment, a precise volume of glucose is injected into a saline-solution filled calibrant source proximate in time to conducting a calibration procedure. The glucose concentration in the source is subsequently calculated based on the measured weight of the saline-solution, as determined prior to glucose injection, and the volume of glucose injected. This method provides a highly accurate and convenient manner for use in a hospital environment. In another embodiment, a premixed calibrant infusion fluid source is provided that includes saline solution and a predetermined concentration of glucose. In such embodiments, shelf life problems related to water evaporation are mitigated by hermetically covering or otherwise hermetically containing the calibrant infusion fluid source up until the point of use. This procedure insures that the glucose concentration in the source is consistent with the concentration at the time of premix.

While the foregoing disclosure discusses illustrative embodiments, it should be noted that various changes and modifications could be made herein without departing from the scope of the described aspects and/or embodiments as defined by the appended claims. Furthermore, although elements of the described aspects and/or embodiments may be described or claimed in the singular, the plural is contemplated unless limitation to the singular is explicitly stated. Additionally, all or a portion of any embodiment may be utilized with all or a portion of any other embodiment, unless stated otherwise.

While certain exemplary embodiments have been described and shown in the accompanying drawings, it is to be understood that such embodiments are merely illustrative of and not restrictive on the broad invention, and that this invention not be limited to the specific constructions and arrangements shown and described, since various other changes, combinations, omissions, modifications and substitutions, in addition to those set forth in the above paragraphs are possible. Those skilled in the art will appreciate that various adaptations and modifications of the just described embodiments can be configured without departing from the scope and spirit of the invention. Therefore, it is to be understood that, within the scope of the appended claims, the invention may be practiced other than as specifically described herein.

What is claimed is:
1. A method for preparing a calibrant infusion fluid source, the method comprising:
   providing a calibrant infusion fluid source that includes a saline solution;
   determining content weight in the calibrant infusion fluid source;

adding a predetermined volume of a predetermined glucose concentrate into the calibrant infusion fluid source; and determining a concentration of glucose in the calibrant infusion fluid source based on the content weight in the calibrant infusion fluid source and the predetermined volume of the predetermined glucose concentrate, wherein a calibration procedure ensues proximate in time to adding the predetermined volume of the predetermined glucose concentrate into the calibrant infusion fluid source.

2. The method of claim 1, wherein providing the calibrant infusion fluid source further comprises providing the calibrant infusion fluid source that includes the saline solution and an anti-clotting agent.

3. The method of claim 2, wherein providing the calibrant infusion fluid source that includes the saline solution and an anti-clotting agent further comprises providing the calibrant infusion fluid source that includes the saline solution and heparin.

4. The method of claim 3, wherein providing the calibrant infusion fluid source that includes the saline solution and heparin further comprises providing the calibrant infusion fluid source that includes about 0.9 percent by weight sodium chloride and 1000 units of heparin sodium salt in 500 ml.

5. The method of claim 1, wherein determining content weight in the calibrant infusion fluid source further comprises weighing the calibrant infusion fluid source and subtracting an empty calibrant infusion fluid source weight from the weight of the calibrant infusion fluid source.

6. The method of claim 1, wherein adding the predetermined volume further comprises injecting the predetermined volume of the predetermined glucose concentrate into the calibrant infusion fluid source.

7. The method of claim 1, wherein injecting the predetermined volume further comprises injecting the predetermined volume of the predetermined glucose concentrate using a syringe having a volume-controlling mechanism.

8. The method of claim 7, wherein injecting the predetermined volume further comprises injecting the predetermined volume of the predetermined glucose concentrate using the syringe having the volume-controlling mechanism, wherein the volume-controlling mechanism is selected from a dimpled stop or a tapered barrel.

9. The method of claim 1, wherein injecting the predetermined volume further comprises injecting the predetermined volume of the predetermined glucose concentrate using a previously un-used syringe.

10. The method of claim 9, wherein injecting the predetermined volume further comprises injecting the predetermined volume of the predetermined glucose concentrate using the previously un-used syringe, wherein the injection is a single injection of the syringe absent a flush.

11. The method of claim 10, wherein adding the predetermined volume further comprises adding the predetermined volume of the predetermined glucose concentrate into the calibrant infusion fluid source, wherein the predetermined volume is based on the predetermined glucose concentrate and the volume of the content in the calibrant infusion fluid source.

12. The method of claim 1, further comprising providing the determined concentration of glucose in the calibrant infusion fluid source to an intravenous blood glucose system.

13. A system for preparing a calibrant infusion fluid source, the system comprising:
    a calibrant infusion fluid source including a saline solution;
    a weighing device operable to determine a weight of the calibrant infusion fluid source a syringe operable to inject a predetermined volume of a predetermined glucose concentrate into the calibrant infusion fluid source; and
    a calculation device operable to calculate a concentration of glucose in the calibrant infusion fluid source based on a content weight in the calibrant infusion fluid source and the predetermined volume of the predetermined glucose concentrate,
    wherein a calibration procedure ensues proximate in time to injecting the predetermined volume of the predetermined glucose concentrate into the calibrant infusion fluid source.

14. The system of claim 13, wherein the calibrant infusion fluid source further comprises the calibrant infusion fluid source including the saline solution and an anti-clotting agent.

15. The system of claim 14, wherein the calibrant infusion fluid source further comprises the calibrant infusion fluid source including the saline solution and heparin.

16. The system of claim 15, wherein the calibrant infusion fluid source including the saline solution and heparin further comprises the calibrant infusion fluid source including about 0.9 percent by weight sodium chloride and 1000 units of heparin sodium salt in 500 ml.

17. The system of claim 13, wherein the calculation device if further operable to determine the content weight in the calibrant infusion fluid source by subtracting an empty calibrant infusion fluid source weight from the weight of the calibrant infusion fluid source including the saline solution.

18. The system of claim 13, wherein the syringe further comprises a volume-controlling mechanism.

19. The system of claim 18, wherein the volume controlling mechanism further comprises a dimpled stop or a tapered barrel.

20. The system of claim 13, wherein the syringe further comprises a previously un-used syringe.

* * * * *